United States Patent
Schwartz et al.

(10) Patent No.: US 10,925,684 B2
(45) Date of Patent: Feb. 23, 2021

(54) CONTACT QUALITY ASSESSMENT BY DIELECTRIC PROPERTY ANALYSIS

(71) Applicant: Navix International Limited, Tortola (VG)

(72) Inventors: Yitzhack Schwartz, Haifa (IL); Eli Dichterman, Haifa (IL); Adi Rabinovich, Modiln (IL)

(73) Assignee: Navix International Limited, Road Town (VG)

( * ) Notice: Subject to any disclaimer, the term of this patent is extended or adjusted under 35 U.S.C. 154(b) by 378 days.

(21) Appl. No.: 15/573,491

(22) PCT Filed: May 11, 2016

(86) PCT No.: PCT/IB2016/052686
§ 371 (c)(1),
(2) Date: Nov. 13, 2017

(87) PCT Pub. No.: WO2016/181315
PCT Pub. Date: Nov. 17, 2016

(65) Prior Publication Data
US 2018/0116751 A1    May 3, 2018

Related U.S. Application Data

(60) Provisional application No. 62/304,455, filed on Mar. 7, 2016, provisional application No. 62/291,065, filed
(Continued)

(51) Int. Cl.
*A61B 18/14*    (2006.01)
*A61B 90/00*    (2016.01)
(Continued)

(52) U.S. Cl.
CPC ............ *A61B 90/06* (2016.02); *A61B 5/0538* (2013.01); *A61B 5/063* (2013.01); *A61B 5/6833* (2013.01);
(Continued)

(58) Field of Classification Search
CPC . A61B 18/1492; A61B 18/1485; A61B 18/12; A61B 18/1206; A61B 2018/00577;
(Continued)

(56) References Cited

U.S. PATENT DOCUMENTS

| 4,917,097 A | 4/1990 | Proudian et al. |
| 5,553,611 A | 9/1996 | Budd et al. |

(Continued)

FOREIGN PATENT DOCUMENTS

| EP | 1504713 | 2/2005 |
| EP | 1726268 | 11/2006 |

(Continued)

OTHER PUBLICATIONS

Communication Relating to the Results of the Partial International Search dated Aug. 22, 2016 From the International Searching Authority Re. Application No. PCT/IB2016/052686.
(Continued)

*Primary Examiner* — Michael F Peffley

(57) ABSTRACT

Devices and methods for assessing tissue contact based on dielectric properties and/or impedance sensing are disclosed. In some embodiments, one or more probing frequencies are delivered via electrodes including an electrode in proximity to a tissue (for example, myocardial tissue). In some embodiments, dielectric parameter values, optionally together with other known and/or estimated tissue characteristics, are measured to determine a contact quality with the tissue. In some embodiments, dielectric contact quality is used, for example, in guiding the formation of a lesion (for
(Continued)

example, RF ablation of heart tissue to alter electrical transmission characteristics).

36 Claims, 13 Drawing Sheets

Related U.S. Application Data on Feb. 4, 2016, provisional application No. 62/160,080, filed on May 12, 2015.

(51) Int. Cl.
*A61B 34/10* (2016.01)
*G16H 50/50* (2018.01)
*G16H 10/60* (2018.01)
*G16H 30/20* (2018.01)
*A61B 34/20* (2016.01)
*A61B 5/0538* (2021.01)
*A61B 5/06* (2006.01)
*A61B 5/00* (2006.01)
*A61B 18/00* (2006.01)
*A61M 25/01* (2006.01)
*A61B 17/00* (2006.01)

(52) U.S. Cl.
CPC .......... *A61B 18/1492* (2013.01); *A61B 34/10* (2016.02); *A61B 34/20* (2016.02); *A61B 90/37* (2016.02); *G16H 10/60* (2018.01); *G16H 30/20* (2018.01); *G16H 50/50* (2018.01); *A61B 90/39* (2016.02); *A61B 2017/00026* (2013.01); *A61B 2018/00357* (2013.01); *A61B 2018/00494* (2013.01); *A61B 2018/00577* (2013.01); *A61B 2018/00642* (2013.01); *A61B 2018/00654* (2013.01); *A61B 2018/00702* (2013.01); *A61B 2018/00732* (2013.01); *A61B 2018/00738* (2013.01); *A61B 2018/00761* (2013.01); *A61B 2018/00791* (2013.01); *A61B 2018/00875* (2013.01); *A61B 2018/00904* (2013.01); *A61B 2034/104* (2016.02); *A61B 2034/105* (2016.02); *A61B 2034/107* (2016.02); *A61B 2034/2046* (2016.02); *A61B 2034/2053* (2016.02); *A61B 2090/065* (2016.02); *A61B 2090/365* (2016.02); *A61B 2090/374* (2016.02); *A61B 2090/3762* (2016.02); *A61B 2090/3983* (2016.02); *A61M 2025/0166* (2013.01)

(58) Field of Classification Search
CPC .. A61B 2018/00875; A61B 2018/0022; A61B 2018/1467; A61B 2018/00357; A61B 2018/00351; A61B 2018/00375; A61B 2018/00684; A61B 2018/00839; A61B 5/053; A61B 5/0538; A61B 5/742; A61B 5/04; A61B 5/72; A61B 5/6852; A62B 2090/065

See application file for complete search history.

(56) References Cited

U.S. PATENT DOCUMENTS

| | | | |
|---|---|---|---|
| 5,598,848 A * | 2/1997 | Swanson | A61B 5/0422 600/508 |
| 5,662,108 A | 9/1997 | Budd et al. | |
| 5,697,377 A | 12/1997 | Wittkampf | |
| 5,724,978 A | 3/1998 | Tenhoff | |
| 5,983,126 A | 11/1999 | Wittkampf | |
| 6,019,725 A | 2/2000 | Vesely et al. | |
| 6,038,468 A | 3/2000 | Rex | |
| 6,240,307 B1 | 5/2001 | Beatty et al. | |
| 6,317,621 B1 | 11/2001 | Graumann et al. | |
| 6,322,558 B1 | 11/2001 | Taylor et al. | |
| 6,515,657 B1 | 2/2003 | Zanelli | |
| 6,640,119 B1 | 10/2003 | Budd et al. | |
| 6,728,562 B1 | 4/2004 | Budd et al. | |
| 6,826,420 B1 | 11/2004 | Beatty et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,187,973 B2 | 3/2007 | Hauck | |
| 7,189,208 B1 | 3/2007 | Beatty et al. | |
| 7,996,060 B2 | 8/2011 | Trofimov et al. | |
| 8,160,690 B2 * | 4/2012 | Wilfley | A61B 5/053 600/547 |
| 8,454,589 B2 * | 6/2013 | Deno | A61B 18/1492 606/34 |
| 9,271,782 B2 * | 3/2016 | Paul | A61B 18/1492 |
| 9,636,164 B2 * | 5/2017 | Panescu | A61B 18/1206 |
| 9,757,191 B2 * | 9/2017 | Avitall | A61B 18/1492 |
| 2002/0068931 A1 | 6/2002 | Wong et al. | |
| 2003/0074011 A1 | 4/2003 | Gilboa et al. | |
| 2003/0220636 A1 | 11/2003 | Bowman et al. | |
| 2004/0039278 A1 | 2/2004 | Wacker et al. | |
| 2004/0044279 A1 | 3/2004 | Lewin et al. | |
| 2004/0097805 A1 | 5/2004 | Verard et al. | |
| 2004/0176804 A1 | 9/2004 | Palti | |
| 2005/0015006 A1 | 1/2005 | Mitschke et al. | |
| 2005/0033164 A1 | 2/2005 | Yatsuo et al. | |
| 2005/0054913 A1 | 3/2005 | Duerk et al. | |
| 2005/0054918 A1 | 3/2005 | Sra | |
| 2005/0245814 A1 | 11/2005 | Anderson et al. | |
| 2007/0043296 A1 | 2/2007 | Schwartz | |
| 2007/0167706 A1 | 7/2007 | Boese et al. | |
| 2007/0167726 A1 | 7/2007 | Unal et al. | |
| 2008/0114235 A1 | 5/2008 | Unal et al. | |
| 2008/0118135 A1 | 5/2008 | Averbuch et al. | |
| 2008/0125775 A1 | 5/2008 | Morris | |
| 2008/0177175 A1 | 7/2008 | Mottola et al. | |
| 2008/0183070 A1 | 7/2008 | Unal et al. | |
| 2008/0208031 A1 | 8/2008 | Kurpad et al. | |
| 2008/0221425 A1 | 9/2008 | Olson et al. | |
| 2008/0275440 A1 | 11/2008 | Kratoska et al. | |
| 2008/0275465 A1 | 11/2008 | Paul et al. | |
| 2009/0015818 A1 | 1/2009 | Ikeda et al. | |
| 2009/0148012 A1 | 6/2009 | Altmann et al. | |
| 2009/0275828 A1 | 11/2009 | Shachar et al. | |
| 2009/0281566 A1 | 11/2009 | Edwards et al. | |
| 2009/0306643 A1 | 12/2009 | Pappone et al. | |
| 2010/0063400 A1 | 3/2010 | Hall et al. | |
| 2010/0217116 A1 | 8/2010 | Eck et al. | |
| 2010/0249579 A1 | 9/2010 | Starks | |
| 2010/0274239 A1 * | 10/2010 | Paul | A61B 18/1233 606/33 |
| 2010/0283484 A1 | 11/2010 | Cohen et al. | |
| 2010/0312094 A1 | 12/2010 | Guttman et al. | |
| 2011/0106221 A1 | 5/2011 | Neal, II et al. | |
| 2011/0230758 A1 | 9/2011 | Eichler | |
| 2012/0059249 A1 | 3/2012 | Verard et al. | |
| 2012/0109115 A1 | 5/2012 | Condie et al. | |
| 2012/0123250 A1 | 5/2012 | Pang et al. | |
| 2012/0172724 A1 | 7/2012 | Hill et al. | |
| 2012/0173217 A1 | 7/2012 | Heimbecher | |
| 2012/0197243 A1 | 8/2012 | Sherman et al. | |
| 2012/0238866 A1 | 9/2012 | Wang et al. | |
| 2013/0137980 A1 | 5/2013 | Waters et al. | |
| 2013/0272593 A1 | 10/2013 | Lee et al. | |
| 2014/0088943 A1 | 3/2014 | Trayanova et al. | |
| 2014/0187949 A1 | 7/2014 | Zhao et al. | |
| 2014/0330111 A1 | 11/2014 | Lichtenstein et al. | |

FOREIGN PATENT DOCUMENTS

| | | |
|---|---|---|
| EP | 2248480 | 11/2010 |
| EP | 2777584 | 9/2014 |
| HR | P20131208 | 3/2014 |
| JP | 2001-340336 | 12/2001 |
| JP | 2009-518130 | 5/2009 |

(56) References Cited

FOREIGN PATENT DOCUMENTS

| JP | 2014-533130 | 12/2014 |
|---|---|---|
| WO | WO 2007/067628 | 6/1997 |
| WO | WO 98/01069 | 1/1998 |
| WO | WO 2007/067628 | 6/2007 |
| WO | WO 2010/102794 | 9/2010 |
| WO | WO 2013/052590 | 4/2013 |
| WO | WO 2016/181315 | 11/2016 |
| WO | WO 2016/181316 | 11/2016 |
| WO | WO 2016/181317 | 11/2016 |
| WO | WO 2016/181318 | 11/2016 |
| WO | WO 2016/181320 | 11/2016 |
| WO | WO 2018/011757 | 1/2018 |

OTHER PUBLICATIONS

Communication Relating to the Results of the Partial International Search dated Aug. 22, 2016 From the International Searching Authority Re. Application No. PCT/IB2016/052688.
Communication Relating to the Results of the Partial International Search dated Aug. 25, 2016 From the International Searching Authority Re. Application No. PCT/IB2016/052692.
Communication Relating to the Results of the Partial International Search dated Aug. 26, 2016 From the International Searching Authority Re. Application No. PCT/IB2016/052687.
International Preliminary Report on Patentability dated Nov. 23, 2017 From the International Bureau of WIPO Re. Application No. PCT/IB2016/052686. (11 Pages).
International Preliminary Report on Patentability dated Nov. 23, 2017 From the International Bureau of WIPO Re. Application No. PCT/IB2016/052687. (10 Pages).
International Preliminary Report on Patentability dated Nov. 23, 2017 From the International Bureau of WIPO Re. Application No. PCT/IB2016/052688. (9 Pages).
International Preliminary Report on Patentability dated Nov. 23, 2017 From the International Bureau of WIPO Re. Application No. PCT/IB2016/052690. (9 Pages).
International Preliminary Report on Patentability dated Nov. 23, 2017 From the International Bureau of WIPO Re. Application No. PCT/IB2016/052692. (13 Pages).
International Search Report and the Written Opinion dated Jan. 3, 2017 From the International Searching Authority Re. Application No. PCT/IB2016/052688. (14 Pages).
International Search Report and the Written Opinion dated Oct. 12, 2016 From the International Searching Authority Re. Application No. PCT/IB2016/052686.
International Search Report and the Written Opinion dated Oct. 16, 2017 From the International Searching Authority Re. Application No. PCT/IB2017/054263. (16 Pages).
International Search Report and the Written Opinion dated Oct. 17, 2016 From the International Searching Authority Re. Application No. PCT/IB2016/052692.
International Search Report and the Written Opinion dated Oct. 21, 2016 From the International Searching Authority Re. Application No. PCT/IB2016/052687. (16 Pages).
International Search Report and the Written Opinion dated Aug. 25, 2016 From the International Searching Authority Re. Application No. PCT/IB2016/052690.
Anter et al. "Evaluation of a Novel High-Resolution Mapping Technology for Ablation of Recurrent Scar-Related Atrial Tachycardias," Heart Rhythm, 13(10): 2048-2055, Oct. 2016.
Arujuna et al. "Acute Pulmonary Vein Isolation Is Achieved by a Combination of Reversible and Irreversible Atrial Injury After Catheter Ablation: Evidence From Magnetic Resonance Imaging", Circulation: Arrhythmia and Electrophysiology, 5(4): 691-700, Published Online May 31, 2012.
Black-Maier et al. "Risk of Atrioesophageal Fistula Formation With Contact-Force Sensing Catheters", HeartRhythm, 14(9): 1328-1333, Published Online Apr. 15, 2017.

Bourier et al. "Electromagnetic Contact-Force Sensing Electrophysiological Catheters: How Accurate Is the Technology?", Journal of Cardiovascular Electrophysiology, 27(3): 347-350, Published Online Jan. 16, 2016.
Bourier et al. "Fiberoptic Contact-Force Sensing Electrophysiological Catheters: How Precise Is Technology?", Journal of Cardiovascular Electrophysiology, 28(1): 109-114, Published Online Oct. 24, 2016.
Chierchia et al. "An Initial Clinical Experience With a Novel Microwave Radiometry Sensing Technology Used in Irrigated RF Ablation for Flutter", Academic Hospital Brussels, Belgium, 1 P. Jan. 1, 2011.
Deno et al. "Measurement of Electrical Coupling Between Cardiac Ablation Catheters and Tissue", IEEE Transactions on Biomedical Engineering, 61(3): 765-774, Published Online Nov. 6, 2013.
Eyerly et al. "The Evolution of Tissue Stiffness at Radiofrequency Ablation Sites During Lesions Formation and in the Peri-Ablation Period", Journal of Cardiovascular Electrophysiology, 26(9): 1009-1018, Sep. 2015.
Gabriel "Compilation of the Dielectric Properties of Body Tissues at RF and Microwave Frequencies", Occupational and Environmental Health Directorate, Radiofrequency Radiation Division, Brooks Air Force Base, Texas, USA, Technical Report for the Period Sep. 15, 1993-Dec. 14, 1994, p. 1-16, Jan. 1996.
Gaspar et al. "Use of Electrical Coupling Information (ECI) in AF Catheter Ablation: A Prospective Randomized Pilot Study", HeartRhythm, 10(2): 176-181, Feb. 2013.
General Electric "CardEP: Streamlined Post-Processing for Enhanced Electrophysiology Procedures", General Electric Company, GE Healthcare, Product Description, 2 P., 2016.
Grace "Modifying PVI Lines to Incorporate Non-PV Targets Identified by Pre-Ablation Mapping with the AcQMap System: Update on the UNCOVER-AF Trial," EP Lab Digest, 17(5), May 2017, 5 pages.
Ikeda et al. "Microwave Volumetric Temperature Sensor Improves Control of Radiofrequency Lesion Formation and Steam Pop", 33rd Annual Scientific Sessions, Heart Rhythm, Boston, MA, USA, May 9-12, 2012, Session: Role of Autonomics in Catheter Ablation, # AB13-05, May 10, 2012.
Ikeda et al. "Novel Irrigated Radiofrequency Ablation Catheter With Microwave Volumetric Temperature Sensor Predicts Lesion Size and Incidence of Steam Pop in Canine Beating Heart", 33rd Annual Scientific Sessions, Heart Rhythm, Boston, MA, USA, May 9-12, 2012, Poster Session III, # PO3-53, May 10, 2012.
Lardo et al. "Visualization and Temporal/Spatial Characterization of Cardiac Radiofrequency Ablation Lesions Using Magnetic Resonance Imaging", Circulation, 102(6): 698-705, Aug. 8, 2000.
Lemola et al. "Computed Tomographic Analysis of the Anatomy of the Left Atrium and the Esophagus. implications for Left Atrial Catheder Ablation", Circulation, 110(24): 3655-3660, Published Online Nov. 29, 2004.
Lunak "12 510(k) FDA Summary for Public Disclosure", St. Jude Medical, Section 12, 6 P., Aug. 29, 2013.
Myronenko et al. "Non-Rigid Point Set Registration: Coherent Point Drift", Advances in Neural Information Processing Systems, NIPS, 19: 1009-1016, 2009.
Pappone "Carto 3", AF-Ablation, Arrhythmology and Cardiac Electrophysiology Department, 1 P., 2009.
Perazzi et al. "Panoramic Video From Unstructured Camera Arrays", Computer Graphics Forum, 34(2): 57-68, May 2015.
Piorkowski et al. "First in Human Validation of Impedance-Based Catheter Tip-to-Tissue Contact Assessment in the Left Atrium", Study of Clinical Results, Poster, Journal of Cardiovascular Electrophysiology, 20(12): 1366-1373, Published Online Jul. 7, 2009.
Sanchez-Quintana et al. "Anatomic Relations Between the Esophagus and Left Atrium and Relevance for Ablation of Atrial Fibrillation", Circulation, 112(10): 1401-1406, Published Online Aug. 29, 2005.
St. Jude Medical "Cardiac Mapping System / ECG. NSite™ NavX™", St. Jude Medical, Products Sheet, 22 P., 2017.

(56) References Cited

OTHER PUBLICATIONS

Vandekerckhove et al. "Flutter Ablation With an Irrigated Catheter Using Microwave Radiometry Sensing Technology: First Report in Men", Sint Jan Hospital, Department of Cardiology, Bruges, Belgium, 1 P., Jan. 1, 2011.
Wang et al. "Microwave Radiometric Thermoetry and Its Potential Applicability to Ablative Therapy", Journal of Interventional Cardiac Electrophysiology, 4(1): 295-300, Feb. 2000.
Wittkampf et al. "LocaLisa: New Technique for Real-Time 3-Dimensional Localization of Regular Intracardiac Electrodes", Circulation, 99(10): 1312-1317, Mar. 16, 1999.
Zhong et al. "On the Accuracy of CartoMerge for Guiding Posterior Left Atrial Ablation in Man", Heart Rhythm, 4(5): 595-602, Published Online Feb. 9, 2007.
Notice of Reasons for Refusal dated Mar. 3, 2020 FRom the Japan Patent Office Re. Application No. 2017-558704 and Its Translation Into English. (14 Pages).
Koruth et al. "Tissue Temperature Sensing During Irrigated Radiofrequency Ablation: A Novel Strategy to Predict Steam Pops", Heart Rhythm, 33rd Annual Scientific Sessions, Boston, MA, USA, May 9-12, 2012, Presentation Abstract, # AB12-02, May 10, 2012.
Sulkin et al. "Novel Measure of Local Impedance Predicts Catheter-Tissue Contact and Lesion Formation", Circulation: Arrhythmia and Electrophysiology, 11(4): e005831-1-e005831-21, Apr. 2018.
Communication Pursuant to Article 94(3) EPC dated 25 Sep. 2020 From the European Patent Office Re. Application No. 16726181.7. (5 pages).
Decision of Refusal Dated Oct. 20, 2020 From the Japan Patent Office Re. Application No. 2017-558704 and Its Translation Into English. (6 pages).

\* cited by examiner

CONTACT QUALITY ASSESSMENT BY DIELECTRIC PROPERTY ANALYSIS

RELATED APPLICATIONS

This application is a National Phase of PCT Patent Application No. PCT/IB2016/052686 having International filing date of May 11, 2016, which claims the benefit of priority under 35 USC § 119(e) of U.S. Provisional Patent Application Nos. 62/160,080 filed on May 12, 2015; 62/291,065 filed on Feb. 4, 2016; and 62/304,455 filed on Mar. 7, 2016. The contents of the above applications are all incorporated by reference as if fully set forth herein in their entirety.

PCT Patent Application No. PCT/IB2016/052686 is also related to PCT Patent Application Nos. PCT/IB2016/052687 titled "SYSTEMS AND METHODS FOR TRACKING AN INTRABODY CATHETER", PCT/IB2016/05268866142 titled "CALCULATION OF AN ABLATION PLAN", PCT/IB2016/052692 titled "FIDUCIAL MARKING FOR IMAGE-ELECTROMAGNETIC FIELD REGISTRATION", and PCT/IB2016/052690 titled "LESION ASSESSMENT BY DIELECTRIC PROPERTY ANALYSIS", all having International filing date of May 11, 2016, the contents of which are incorporated herein by reference in their entirety.

FIELD AND BACKGROUND OF THE INVENTION

The present invention, in some embodiments thereof, relates to systems and methods for probe positioning within a body cavity, and more particularly, but not exclusively, assessment of contact between an intra-body electrode and a body cavity surface.

RF ablation probes are in use for minimally invasive ablation procedures, for example, in the treatment of cardiac arrhythmia. A high frequency alternating current (e.g., 350-500 kHz) is introduced to a treatment region through the probe, creating an electrical circuit involving tissue, which heats up as it absorbs energy of the applied electrical field. The heating results in effects such as tissue ablation. In the control of cardiac arrhythmia, a goal of ablation is to create lesions in a pattern which will break pathways of abnormal electrophysiological conduction which contribute to heart dysfunction (such as atrial fibrillation).

One variable affecting the heating is the frequency-dependent relative permittivity K of the tissue being treated. The (unitless) relative permittivity of a material (herein, K or dielectric constant) is a measure of how the material acts to reduce an electrical field imposed across it (storing and/or dissipating its energy). Relative permittivity is commonly expressed as $$\kappa = \varepsilon_r(\omega) = \frac{\varepsilon(\omega)}{\varepsilon_0},$$

where $\omega = 2\pi f$, and f is the frequency (of an imposed voltage or signal). In general, $\varepsilon_r(\omega)$ is complex valued; that is: $\varepsilon_r(\omega) = \varepsilon'_r(\omega) + i\varepsilon''_r(\omega)$.

The real part $\varepsilon'_r(\omega)$ is a measure of energy stored in the material (at a given electrical field frequency and voltage), while the imaginary part $\varepsilon''_r(\omega)$ is a measure of energy dissipated. It is this dissipated energy that is converted, for example, into heat for ablation. Loss in turn is optionally expressed as a sum of dielectric loss $\varepsilon''_{rd}$ and conductivity $\sigma$ as $$\varepsilon''_r(\omega) = \varepsilon''_{rd} + \frac{\sigma}{\omega \cdot \varepsilon_0}.$$

Any one of the above parameters: namely κ, ε, $\varepsilon'_r$, $\varepsilon''_r$, σ, and/or $\varepsilon''_{rd}$, may be referred to herein as a dielectric parameter. The term dielectric parameter encompasses also parameters that are directly derivable from the above-mentioned parameters, for example, loss tangent, expressed as tan $$\sigma = \frac{\varepsilon''_r}{\varepsilon'_r},$$

complex refractive index, expressed as $n = \sqrt{\varepsilon_r}$, and impedance, expressed as $$Z(\omega) = \sqrt{\frac{i\omega}{\sigma + i\omega\varepsilon_r}}$$

(with $i = \sqrt{-1}$).

Herein, a value of a dielectric parameter of a material may be referred to as a dielectric property of the material. For example, having a relative permittivity of about 100000 is a dielectric property of a 0.01M KCl solution in water at a frequency of 1 kHz, at about room temperature (20°, for example). Optionally, a dielectric property more specifically comprises a measured value of a dielectric parameter. Measured values of dielectric parameters are optionally provided relative to the characteristics (bias and/or jitter, for example) of a particular measurement circuit or system. Values provided by measurements should be understood to comprise dielectric properties, even if influenced by one or more sources of experimental error. The formulation "value of a dielectric parameter" is optionally used, for example, when a dielectric parameter is not necessarily associated with a definite material (e.g., it is a parameter that takes on a value within a data structure).

Dielectric properties as a function of frequency have been compiled for many tissues, for example, C. Gabriel and S. Gabriel: *Compilation of the Dielectric Properties of Body Tissues at RF and Microwave Frequencies* (web pages presently maintained at www://niremf(dot)ifac(dot)cnr(dot)it/docs/DIELECTRIC/home(dot)html).

Dielectric properties comprise certain measured and/or inferred electrical properties of a material relating to the material's dielectric permittivity. Such electrical properties optionally include, for example, conductivity, impedance, resistivity, capacitance, inductance, and/or relative permittivity. Optionally, dielectric properties of a material are measured and/or inferred relative to the influence of the material on signals measured from electrical circuits. Optionally, dielectric properties of a material are measured and/or inferred relative to the influence of the material on an applied electric field. Measurements are optionally relative to one or more particular circuits, circuit components, frequencies and/or currents.

Microscopically, several mechanisms potentially contribute to electrically measured dielectric properties. For example, in the kHz-MHz range, movement of ionic charge carriers generally dominates. In many tissues, cellular membranes play a significant role in the compartmentalization of ionic charges. Conductance pathways are also potentially influenced by the cellular structure of a tissue. Dielectric properties optionally are influenced by and/or take into account non-dielectric properties such as temperature.

SUMMARY OF THE INVENTION

There is provided, in accordance with some exemplary embodiments, a method of characterizing contact quality of an intra-body probe with a target tissue, comprising: measuring dielectric properties of the environment of an electrode of an intra-body type electrode using an electrical circuit, the electrical circuit being defined by the electrode placed intra-bodily so that the target tissue is included in the electrical circuit; and characterizing contact between the probe and the target tissue, wherein the characterization of the contact comprises mapping of the measured dielectric properties to a mapped value within a range of values characterizing the contact quality.

According to some embodiments, the mapped value comprises an index characterizing contact quality.

According to some embodiments, the mapped value represents a contact force equivalent, such that a force of contact of the intra-body probe with the target tissue is represented by the mapped value.

According to some embodiments, the range of values characterizing the contact quality comprises at least four possible values.

According to some embodiments, the intra-body probe comprises an ablation electrode configured for ablation of the target tissue.

According to some embodiments, the ablation electrode comprises the electrode defining the electrical circuit.

According to some embodiments, the characterizing comprises evaluating sufficiency of the contact for effective lesioning by the ablation electrode.

According to some embodiments, the method comprises providing a user feedback indicating the sufficiency of contact for effective lesioning.

According to some embodiments, the ablation electrode is configured for the formation of a lesion in the target tissue by at least one of the group consisting of: thermal ablation, cryoablation, RF ablation, electroporating ablation, and/or ultrasound ablation.

According to some embodiments, the method comprises operating an ablation electrode based on the characterization of the contact.

According to some embodiments, the operating of the ablation electrode is gated to occur only when the characterized contact is within a predetermined range.

According to some embodiments, the characterizing contact is performed iteratively during operating of the ablation electrode.

According to some embodiments, the operating of the ablation electrode is based on an estimated contact force of the characterized contact, such that at least one of an ablation power, a duration of ablation, a selection of an electrode, and a frequency of ablation energy, is selected based on the estimated contact force.

According to some embodiments, the characterizing comprises estimation of an equivalent force of contact of the probe with a surface of the target tissue.

According to some embodiments, the estimation of an equivalent force of contact is substantially independent of an angle of contact between the probe and the surface of the target tissue.

According to some embodiments, the characterizing comprises evaluating a risk of perforation of the target tissue by the probe.

According to some embodiments, the method comprises providing a user feedback indicating the risk of perforation.

According to some embodiments, the method comprises moving the probe under automated control based on the characterization of the contact.

According to some embodiments, the target tissue comprises cardiac tissue.

According to some embodiments, the target tissue comprises cardiac tissue of the right atrium.

According to some embodiments, the intra-body probe makes a plurality of simultaneous contacts with the target tissue, and the characterizing comprises separately characterizing each of the plurality of simultaneous contacts.

According to some embodiments, the intra-body probe comprises an ablation electrode, and wherein the method comprises operating the ablation electrode to ablate at each of the plurality of simultaneous contacts under separate control, based on the corresponding characterizing of contact.

According to some embodiments, the separate control comprises delivery of a separately selected at least one of a frequency, phase, or level of ablation power to each of the plurality of simultaneous contacts.

According to some embodiments, the separate control comprises separately selected timing of delivery of ablation power to each of the plurality of simultaneous contacts.

According to some embodiments, the characterizing of contact is based on a data structure mapping measured dielectric properties to a characterization of contact with the target tissue.

According to some embodiments, the character of contact comprises at least one from among the group consisting of: a risk of perforating the tissue with the intra-body probe, an estimate of contact force applied to the tissue by the intra-body probe, and/or an assessment of adequate contact for reliable ablation using the intra-body probe.

According to some embodiments, the data structure comprises machine-learned associations applicable to the measured dielectric properties to convert them to the characterization of contact with the target tissue.

According to some embodiments, the dielectric properties comprise dielectric properties measured for a plurality of electrical field frequencies.

According to some embodiments, the electrical field frequencies are in a range between about 5 kHz and about 20 kHz.

There is provided, in accordance with some exemplary embodiments, a device for ablation of a target tissue based on dielectric contact quality of an intra-body ablation probe with the target tissue, comprising: the intra-body ablation probe, including at least one electrode; an electrical field measurement device, configured to measure dielectric properties in the environment of the at least one electrode based on signals sensed by the at least one electrode; and a contact characterization module, configured to characterize contact between the intra-body ablation probe and the target tissue, based on the dielectric properties measured by the electrical field measurement device.

According to some embodiments, the contact characterization module comprises a data structure mapping the dielectric properties to characterization of contact.

According to some embodiments, the device comprises a display configured to display the characterized contact as an estimate of contact force.

There is provided, in accordance with some exemplary embodiments, a method of indicating the orientation of a displayed view of an anatomical structure, comprising: displaying on a display an anatomical view of the anatomical structure in a user-adjustable orientation; and coordinating an orientation of a displayed schematic representation of a portion of the anatomical structure to the user-adjustable orientation of the anatomical view, such that the schematic representation is displayed in the same orientation as the anatomical view of the anatomical structure; wherein the schematic representation comprises a body portion representing a first part of the anatomical structure, and a plurality of protruding portions representing protruding portions of the anatomical structure and protruding from the body portion, such that the orientation of the plurality of protruding portions is identifiable from any orientation of the displayed schematic representation.

According to some embodiments, the anatomical structure comprises an atrium of a heart.

According to some embodiments, the body portion of the schematic representation comprises at least two sub-portions; each sub-portion being distinctively shaded, and corresponding to a predetermined portion of the anatomical structure.

According to some embodiments, the anatomical view of the anatomical structure includes a view of at least one obscuring anatomical portion positioned to obscure the predetermined portions of the anatomical structure, and wherein the schematic representation omits to represent this obscuring anatomical portion, thereby preventing obscuring of the at least two portions of the schematic representation.

According to some embodiments, each of the at least two sub-portions of the schematic representation corresponds to an atrium of a heart, and the plurality of protruding portions comprise a plurality of generally cylindrical protrusions corresponding to the number of veins feeding into each atrium.

According to some embodiments, the plurality of protruding portions comprise a protrusion indicating a position of a heart valve.

There is provided, in accordance with some exemplary embodiments, a method of characterizing contact quality of an intra-body probe with a target tissue, comprising: measuring dielectric properties of the environment of an electrode of an intra-body type electrode using an electrical circuit, the electrical circuit being defined by the electrode placed intra-bodily so that the target tissue is included in the electrical circuit; and characterizing contact between the probe and the target tissue, wherein the characterization of the contact comprises conversion of the measured dielectric properties to an equivalent contact force estimation, and wherein the estimation of an equivalent force of contact is substantially independent to an angle of contact between the probe and the surface of the target tissue.

According to some embodiments, the substantial independence comprises a change of less than 10% through a range of angles of contact, and the range of angles of contact is within 45° of a central angle of contact.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit", "module" or "system". Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
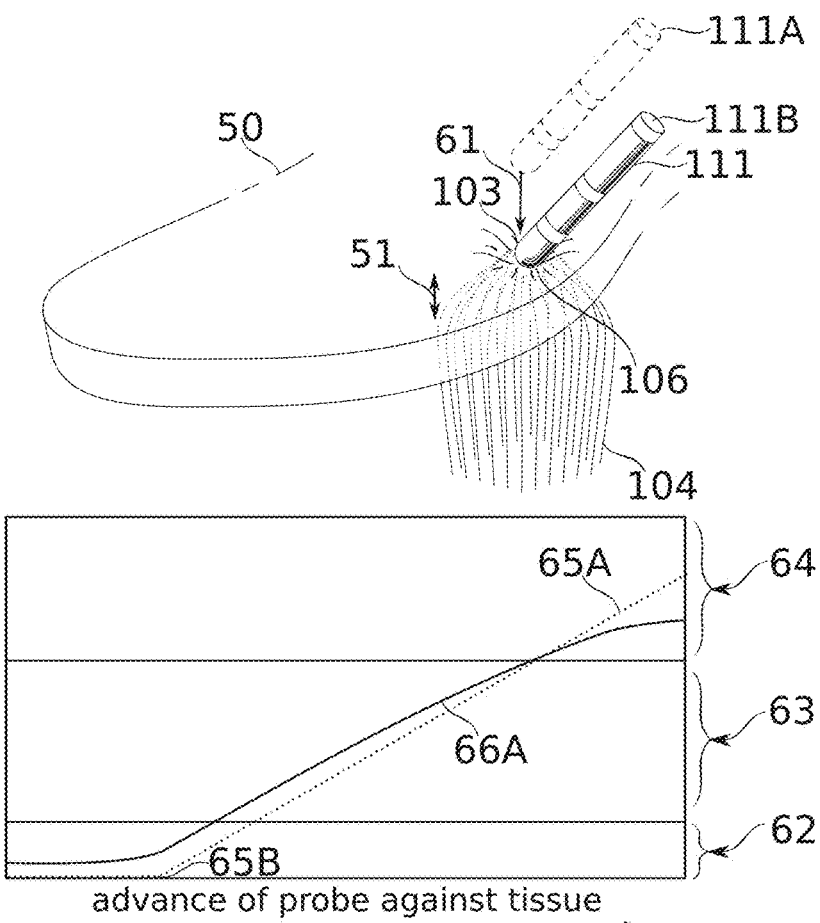
FIG. 1A schematically represents a catheter probe being brought into contact with a tissue wall for measurement of a dielectric contact quality therebetween, according to some embodiments of the present disclosure.

The present invention, in some embodiments thereof, relates to systems and methods for probe positioning within a body cavity, and more particularly, but not exclusively, assessment of contact between an intra-body electrode and a body cavity surface.

Overview

An aspect of some embodiments of the present invention relates to evaluation of contact between an electrode and a tissue surface based on multi-parameter dielectric property measurements. In some embodiments, the electrode is intra-body (for example, an electrode introduced into the body over a catheter), and the tissue surface is an internal surface, for example, the wall of a heart, or of another organ such as a lumen of the digestive tract (e.g., the stomach).

In some embodiments, dielectric property measurements include sampling of electrical signals affected by dielectric properties in the environment surrounding the intra-body electrode. Movement of the intra-body electrode, and in particular, movement that affects a degree of contact with an internal surface of a target tissue, changes this environment, leading to changes in measured dielectric properties. In some embodiments, the evaluated contact is converted to and/or expressed as a dielectric contact quality, for example as a value from along a dielectric contact quality scale.

For certain applications comprising transcatheter delivery of a disease treatment, it is a potential advantage to distinguish between different degrees of contact between a probe which delivers the treatment, and tissue being treated. Degree of contact potentially affects treatment results; for example, by affecting the coupling of energy transfer between a treatment probe and target tissue. For embodiments in which a treatment relies on energy transfer (heating or cooling, for example) "contact quality per se" refers to how the various physical correlates of degree of contact (e.g., contact surface area and/or microscopic distances between surfaces approaching one another) influence such coupling. Actual measures of parameters affected by contact, including, for example, contact force and dielectric contact quality, may in turn be understood as measures of contact quality which estimate contact quality per se, and thus also, for example, are optionally used as predictors of a probe-delivered procedure's effectiveness.

In some embodiments of the invention, electromagnetic signals indicative of dielectric properties of an electrode's environment are converted into one or more measures of contact quality. In some embodiments, the conversion comprises a mapping from measurements of a plurality of dielectric properties to a mapped value. Herein, such a dielectric property-derived measure of contact quality is referred to as a measure of "dielectric contact quality" (that is, a contact quality which is dielectrically derived). Optionally, dielectric properties are determined by analysis of multidimensional signals (e.g. indicative of impedance characteristics of tissue nearby (including contacting) a sensing electrode. The signals carry information indicative, for example, of imaginary and/or real components of impedance as a function of a plurality of electrical field frequencies.

Optionally, these multidimensional signals are converted to a simpler (e.g., lower-dimensional, for example, single-dimensional) representation as a value on a scale of dielectric contact quality. In some embodiments, dielectric contact quality is expressed as a category expressing a character of contact (sufficient, insufficient, and/or excessive contact, for example), and/or as a numerical value which characterizes contact, the characterizing value being with or without units (e.g., 20%, 10 grams-force, a scale of integers, etc.). In some embodiments, at least four different levels of dielectric contact quality are identified. Optionally, at least two levels of sufficient contact (sufficient for performance of an ablation or other procedure, for example) are distinguished. In some current practice, contact force (as measured, for example, by a piezoelectric force sensor) is used as a standard for estimating a contact quality per se. In some embodiments of the present invention, a quality of contact is expressed as a contact force equivalent. For example, a certain contact quality is optionally expressed in units of gram-force which correlate with units of gram-force actually exerted by the contact, even though the actual measurement is optionally by the analysis of signals which are not of contact force.

Use of contact force measured by an ablation probe force sensor has been introduced in the prior art for ablation treatment (by RF ablation, for example) of atrial fibrillation (AF). Ablation performed in this treatment approach seeks to abolish atrial fibrillation by cutting (at the point of ablation) conduction pathways leading between regions of impulse initiation and contractile myocardial tissue. For example, ablation is optionally performed to cut off sites of electrical impulse generation in or near the pulmonary veins (PV) from the rest of the heart.

AF can recur, for example, in about 50% of patients after ablation, with the majority of recurrences (about 95%, for example) being associated with the restoration of a conductive pathway leading from a pulmonary vein (PV reconnection). Use of contact force measurement to guide ablation has led to an apparent reduction in PV reconnection. Nevertheless, it has been observed that the efficacies of some alternative 'cut and sew' (Cox-MAZE) methods of interrupting conduction pathways continue to exceed that of catheter-based AF ablation, even using contact force as a guide. Moreover, current methods of contact force measurement rely on specialized probes comprising a force sensor.

Dielectric contact quality offers some potential advantages over contact force as an estimator of contact quality per se. For example, the impedance of an electrical circuit comprising tissue near the contact between the probe and the tissue may be indicative of electromagnetic coupling affecting the transfer of ablation energy between a probe and tissue. As a measure of electromagnetic coupling, contact force measurement is potentially a more indirect indication than dielectric contact quality. Also for example, it is a potential advantage for directness of measurement to use the same electrode for both contact sensing and ablation (this is possible, for example, when using RF ablation). Furthermore, it is a potential advantage to be able to obtain a measure of contact quality using a probe that lacks a special additional force sensor. In some embodiments, a multi-electrode probe is provided; e.g., a probe comprising a plurality of electrodes arranged along a longitudinal extent of the probe. Optionally, the electrodes are arranged on the probe (for example, the probe may be flexible) so that they can be brought into simultaneous contact with a tissue surface. In some embodiments, each of the plurality of electrodes is separately operable for determination of a corresponding dielectric contact quality. This is a potential advantage for multi-electrode applications, since it may be prohibitively difficult to provide each electrode with its own corresponding force sensor.

An aspect of some embodiments of the present invention relates to the representation of dielectrically measured contact quality between an electrode and a tissue surface as a force-unit equivalent. In some embodiments, a displayed indication of dielectric contact quality is presented to a user as an estimated equivalent value in units of force. This is a potential advantage for allowing dielectric contact quality results to be referenced to a device-independent standard. For example, tissue contact guidelines in a protocol for treatment (e.g., tissue ablation) are optionally provided in terms of a unit of force such as grams-force, Newtons, millinewtons, or another standard unit.

In some embodiments, a calibration scale allowing the translation form dielectric contact quality to contact force is obtained from training trials in which contact force is directly observed in conjunction with dielectric contact quality measurement.

In some embodiments, a display of dielectric contact quality comprises two or more complementary displays; for example, a graphical bar display allowing at-a-glance (optionally, peripherally viewed) judgment of general contact status, together with one or more numeric indications suitable to direct comparison with protocol guidelines.

An aspect of some embodiments of the present disclosure relates to the use of a graphical user interface (GUI) widget for representation of an organ orientation in a 3-D space. In some embodiments, the organ is a heart, or portion of heart anatomy, for example, atria of a heart.

In some embodiments, a mutable 3-D view of an organ's anatomy is presented to a user for use in tasks such as procedure planning, probe navigation and/or probe positioning. The 3-D view is optionally mutable in one or more of a numerous respects including not only orientation, but also (for example) color, completeness, texture, transparency, and/or scale. This mutability provides a potential advantage for rich visual presentation of information. For example, regions of interest can be magnified for detailed work; color mappings are optionally used to represent physiological parameters such as tissue vitality and/or thickness. However, mutable display also creates a risk of cognitive overload which potentially leads to operator disorientation, distraction, and/or fatigue. A sense of spatial orientation in particular can be difficult to continually maintain, yet awareness of orientation is potentially crucial to the success of a procedure comprising navigation of a catheter probe through complex and/or constraining anatomical structures.

In some embodiments, a GUI widget representative of the features of an organ is provided for coordinated display with a 3-D view of an organ's anatomy. The coordination, in some embodiments, comprises coordinated adjustment of the orientation of the GUI widget to the orientation of the anatomical view, such that knowing the orientation of the GUI widget uniquely determines the 3-D orientation of the anatomical view. The GUI widget is optionally manipulated by user input directed at the GUI widget itself, and/or updated to reflect user input directed at another control (for example, sliders, buttons, and/or the anatomical view display itself).

Optionally, the GUI widget is comprised of simple geometrical shapes which suggest (without literally depicting) anatomical landmarks of the true anatomy. Optionally, the landmarks which are shown are those most salient to treatment and/or diagnostic activities that the anatomical display is supporting. For example, blood vessels which mark navigation pathways and/or treatment zones are optionally shown as cylindrical tubes. Complex shapes (such as the atria and valves) are optionally reduced to a small number of salient visual indications, such as position and/or relative size. GUI widget representation of anatomical structures peripheral to an operator's activities (for example, the ventricles) are optionally suppressed altogether. Such a GUI widget provides a potential advantage in striking a balance between two opposing constraints: being visually stable and simple enough that orientation is instantly identifiable to a device operator, yet being enough similar to actual anatomy that orientation homology is directly apparent.

Optionally, one or more indications of anatomical structures separate from the displayed anatomy are provided for indication of orientation. For example, a cylinder showing the relative position of the esophagus (which can potentially be at risk for damage during ablation) is optionally displayed near a schematic model of the atria. In some embodiments, a portion of a lumen of the digestive tract (e.g., a stomach) is schematically represented. Optionally, orientation is indicated by cylinders representing entrance and exit passages from the represented tissue. Optionally, orientation is indicated by a schematic representation of the position of a characteristic bend of a lumenal structure, for example: a bend of a large intestine or an arch of an aorta.

In some embodiments, a GUI widget is adjustable in one or more characteristics additional to orientation. For example, view scale is optionally indicated by marking of anatomical view regions on the GUI widget. Optionally, internal anatomy views (as is from within an atrium for example) are distinguished from external anatomy views. This is performed, for example, by visually cutting away a portion of the GUI widget so that its modeled interior is seen.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Dielectric Contact Quality

Figure 3:
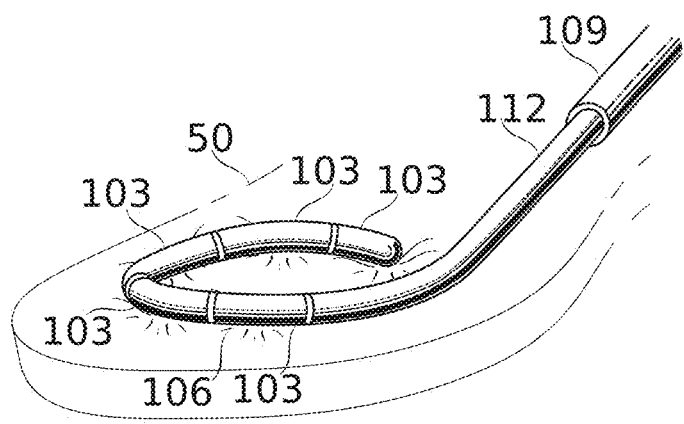
FIG. 3 schematically illustrates a catheter-deployed probe comprising a plurality of electrodes configured for sensing of dielectric contact quality, according to some embodiments of the present disclosure.

Reference is now made to FIG. 1A, which schematically represents a catheter probe 111 being brought into contact with a tissue wall 50 for measurement of a dielectric contact quality therebetween, according to some embodiments of the present disclosure. Reference is also made to FIG. 3, which schematically illustrates a catheter-deployed multi-electrode probe 112 comprising a plurality of electrodes 103 configured for sensing of dielectric contact quality, according to some exemplary embodiments of the present disclosure.

In some embodiments, at least one electrode 103 of a catheter probe 111, 112 is configured for use in producing a time-varying electrical field 104 across tissue wall 50 (a second electrode used in field production not shown), while the probe 111, 112 approaches and is forced into contact with a tissue contact region 106. In some embodiments, each individual electrode 103 of multi-electrode probe 112 optionally separately defines a tissue contact region 106. Electrodes 103 of multi-electrode probe 112 are optionally operated to produce an electrical field between pairs of electrodes 103, and/or between an electrode 103 and an electrode positioned remotely. Electrode 103 is also configured for the measurement of signals from the time-varying electrical field 104 which reflect the dielectric properties of the electrode's environment. In some embodiments, these signals change as the probe 111 is moved through a distance 61, for example, from position 111A to position 111B. In particular, signals received potentially change significantly during movement between an initial contact of probe 111 with tissue contact region 106, and a later contact wherein probe 111 has been further forced against tissue contact region 106.

Herein, tissue ablation from a probe provides an example of a probe-delivered, contact quality-dependent procedure. It is to be understood that other probe contact quality-dependent procedures are also included within the scope of this disclosure; for example, contact as a preliminary to biopsy sampling.

In some embodiments, probe 111 (optionally electrode 103 itself) is adapted for use to ablate tissue at contact region 106. The outcome of such ablation, and in particular RF ablation, has been found to significantly depend on how contact is formed between the ablation probe and the tissue. Optionally, for example, a degree of contact coupling between an ablation probe and target tissue affects how energy is transferred between them to produce ablation. Dielectric assessment of contact also provides a potential advantage in evaluation of data applicable to other dielectric measurement modalities. For example, the validity of dielectric tissue state assessment (e.g., lesion extent and/or continuity, tissue edema) is optionally verified at least in part by confirmation of a minimum quality of contact by the electrode used for measurement.

In some embodiments, other electrodes, another catheter probe and/or another ablation method is used in a procedure, for example, cryoablation, ultrasound ablation, laser ablation, electroporating ablation, or another form of ablation. In such instances, coupling of contact quality sensed by electrode 103 to effective contact by the portion of the probe comprising an element which is actuated to perform a treatment procedure is optionally obtained, for example, by putting both electrode 103 and the treatment element on the same probe. Optionally, the contact sensing electrode and the procedure administrating portion (e.g., lesioning element) of the probe are positioned, for example, alongside each other, encircling one another, and/or interpenetrating one another at a contact surface. Additionally or alternatively, a contact offset between the two probe elements is accounted for in calibration. In some embodiments, a plurality of probes (e.g., one carrying the contact sensing electrode, and one carrying the procedure administrating portion) are positioned in tandem so that a sensed dielectric contact quality from a first probe provides useful information about the contact quality of a second probe.

In some embodiments, a plurality of electrodes 103 on a multi-electrode probe 112 used in sensing of dielectric contact quality are optionally operable for treatment (e.g., lesioning) and/or assessment of treatment result (dielectric assessment of treatment results, e.g., lesion characteristics, is described, for example, in U.S. Provisional Patent Application No. 62/291,065 to the applicant, the contents of which are incorporated herein by reference in their entirety. For example, probe 112 is optionally flexible (e.g., into a loop shape as shown in FIG. 3) to assume the shape of a portion of an extended train of tissue lesion foci, allowing electrodes 103 to be positioned therealong. Assessment of contact quality for each electrode provides a potential advantage by allowing the selective operation of electrodes in good contact for ablation and/or dielectric tissue assessment, reducing the potential for ineffective treatment and/or spurious results due to lack of quality contact at one or more of the electrode positions.

In some embodiments, evaluation of contact quality comprises categorization of contact quality. For example, a distinction is made between contact which is sufficient for successful ablation, and contact which is insufficient. In some embodiments, contact force large enough to create a potential risk of tissue perforation is distinguished as another category. Optionally, contact quality comprises a quantitative evaluation; for example, ordered (optionally, continuous) gradations between and/or within each category of contact.

In some embodiments of the invention, signals and/or their changes indicative of dielectric properties of the environment of electrode 103 are converted into one or more measures of contact quality. The conversion optionally involves dimensional reduction of the inputs from which contact quality is derived.

For example, impedance measurements used as inputs of this conversion are optionally multidimensional (impedance measurements are used, in some embodiments, as indications of dielectric properties). An impedance measurement may comprise an impedance value for each of a plurality of frequencies. Each impedance value may have a real part and/or an imaginary part, which may be considered a dimension of the input.

Parameters that affect signals indicative of dielectric properties may include, for example, not only contact quality, but also aspects of other elements of the contact quality measurement circuit, for example:

The configuration of circuit elements including the probe 111 and/or electrode 103 itself;

The dielectric properties of tissue including tissue wall 50, tissue contact region 106, and/or other tissue (such as body tissue 102 of FIG. 1G) in which electrical field 104 is established; and The configuration of other circuit elements, for example, skin patches 105 (FIG. 1G), leads, and other electrical components of a dielectric measurement system.

Nevertheless, the inventors have surprisingly found it possible to determine a correspondence (by correlation, for example) between multidimensional dielectric measurements and one or more other measures of contact quality.

Insofar as force-measuring probes are currently available and in use, contact force measurement provides a preferred example of a reference against which calibration of dielectric contact quality is optionally performed. However, estimation of contact quality based on dielectric measurements is not limited to comparisons with contact force measurements. For example, results of dielectric measurements may be correlated with (or calibrated against) direct measurements of procedure results (e.g., ablation effectiveness). Optionally, a measure of contact quality comprises a combined assessment of dielectric contact quality and contact force as measured by a force-sensing probe. For example, optionally, an anticipated procedure result is jointly predicted by sensed force and dielectric contact quality.

In some embodiments of the current invention, there is a correspondence determined between dielectric measurements, and the force with which a probe 111 bearing an electrode 103 is pushed into a tissue contact region 106. Herein, such a determined correspondence is called a scale of dielectric contact quality. Contact force can be directly measured, for example, from the deformation of a piezoelectric device mounted to a specialized force-measuring catheter probe.

Optionally, correspondence is determined by means of a calibration procedure. The calibration procedure comprises, for example, simultaneously measuring both dielectric properties and contact forces in a number of calibration experiments (for example, 100, 1000, 10000, or another larger or intermediate number of calibration experiments). Optionally, calibration experiments are performed with an ex vivo preparation of the target tissue of interest; for example, a preparation of myocardial tissue when dielectric contact quality with heart wall tissue is to be determined. Additionally or alternatively, calibration comprises measuring dielectric properties from a probe during a procedure and corresponding experimental and/or actual procedure results (for example, ablation lesion results). From these data, a dielectric contact quality scale is determined in some embodiments; for example, by use of statistical analysis, machine learning, and/or another technique for extracting associations from multivariate data. In some embodiments, further information is used; for example, anatomical data (e.g., general atlas data, and/or data personalized to the patient) and/or probe position data. Optionally, this further information serves to affect how a scale is applied, for example, by providing values of parameters affecting dielectric contact quality determination. Optionally, relationships established by the calibration procedure are provided as data structure 130 of a contact quality assessing system 100, for example, as described in relation to FIG. 1G. Optionally, data structure 130 comprises a mapping between a plurality of dielectric measurement results, and a corresponding plurality of values along a contact quality scale. The contact quality scale is optionally one dimensional. Optionally the scale is expressed in units equivalent to force. Additionally or alternatively, it is expressed in terms of an arbitrary unit (for example, a one or two digit value on a relative scale).

In some embodiments, a contact quality assessing system 100 includes calibration data (for example, data structure 130) for a plurality of different probe 111 and/or electrode 103 types. The calibration data for use is optionally selected based upon identification of the probe 111 and/or electrode 103 type. In some embodiments a probe 111 and/or electrode 103 is provided together with calibration data (for example, data structure 130) which can be in turn provided to contact quality assessing system 100 for use. Optionally, the calibration data is individualized to the provided probe 111 and/or electrode 103. In some embodiments, a calibration phantom is provided which allows at least partial recalibration of probe 111 and/or contact electrode 103. For example, the calibration phantom optionally comprises a mount for probe 111, and a force sensor which measures the force with which electrode 103 presses against a phantom tissue which is part of the calibration phantom (for example, a fluid-filled bag, a polymer membrane, and/or another artificial substitute for contacted tissue). Optionally, force and/or dielectric property measurements made using the calibration phantom are used as indications to adjust use of data structure 130 so that contact quality assessments are calibrated for the particular configuration of the contact quality assessing system 100.

Figure 1B:
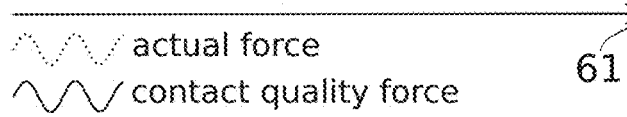
FIG. 1B is a simplified and schematic plot of contact force and dielectric contact quality as a function of advancement of probe against tissue wall, according to some embodiments of the present disclosure.

Reference is now made to FIG. 1B, which is a simplified and schematic plot of contact force and dielectric contact quality as a function of advancement of probe 111 against tissue wall 50, according to some embodiments of the present disclosure.

Arrow 61 represents the motion 61 of FIG. 1A. Dotted line 65A represents a direct force generated between the probe 111 and the tissue contact region 106. Initially (e.g., up to inflection point 65B), this force is substantially zero. It begins to rise on initial contact, and continues to rise until the end of the graph. The rise of force as a function of distance is simplified to a linear relationship for purposes of illustration. Also in the example of FIG. 1B, and during the same advancement of probe 111 into tissue, dielectric measurements are optionally taken. Solid line 66A represents the evolution of a measure of contact quality which these dielectric measurements comprise (the conversion being performed, for example, as determined by a previous calibration procedure).

While the two measures (e.g., of direct contact force and of dielectric contact quality) are not necessarily linearly related throughout the calibration range, there are, in some embodiments, three regions in particular which can be assigned a qualitative functional significance. Region 62 of FIG. 1B is a low-contact region of the graph, optionally defined as a region of the graph within which there is an elevated risk of failure for a procedure (an ablation procedure, for example) performed at that level of contact. Region 64 is an excessive-contact region of the graph, optionally defined as a region of the graph within which there is an elevated risk of perforation by probe 111, and/or other mechanical trauma. Region 63 represents an intermediate region of contact quality within which procedure success (ablation procedure success, for example) is predicted.

As represented, the relationship between contact force and contact quality is approximately linear in the predicted success range 63 (a non-linear relationship is also possible). Optionally, there are larger deviations from linearity in range 64 and/or range 62. This is shown also in the data-derived example of actual vs. estimated contact force of FIG. 5. The deviation (apparent loss of sensitivity, for example) is not necessarily a practical limitation of the dielectric method: the extreme ranges anyway are optionally considered as "avoided regions" for purposes of treatment. Moreover, it should be understood that contact force, though optionally used as a reference standard (for example, as a guide in actual clinical practice), itself is a proxy for contact quality per se as defined hereinabove. Potentially, dielectric contact quality is a predictor of procedure results comparable to, or even better than contact force.

Figure 1C:
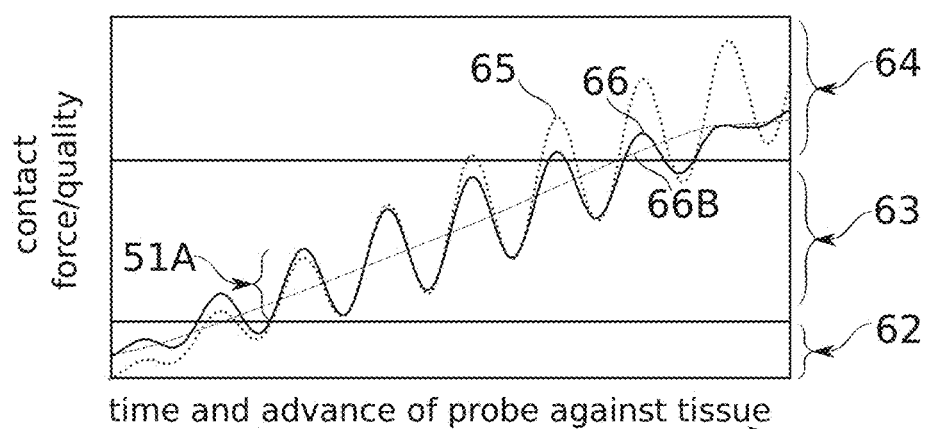
FIG. 1C is a simplified and schematic plot of contact force and dielectric contact quality as a function of time and advancement of probe against a cyclically moving tissue wall, according to some embodiments of the present disclosure.
Figure 1C:
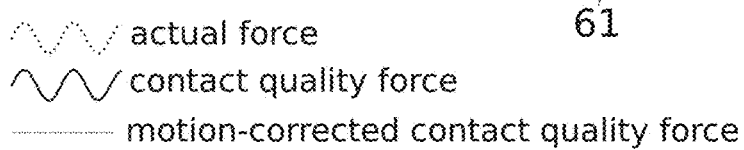

Reference is now made to FIG. 1C, which is a simplified and schematic plot of contact force and dielectric contact quality as a function of time and advancement of probe 111 against a cyclically moving tissue wall 50, according to some embodiments of the present disclosure.

The features of FIG. 1C are generally the same as for FIG. 1B, with the exception that a cyclical motion 51 of tissue wall 50 has been introduced. This is a typical situation, for example, when applying a probe to a heart wall. In some embodiment of the invention, dielectric contact quality is measured as part of a tissue ablation procedure by means of an ablation probe applied to a heart wall (an atrial wall, for example). Physiological motion (for example, the beating of the heart and/or respiration) potentially produces time-varying contact quality (indicated, for example, by range 51A). Plots of both contact force 65 and dielectric contact quality 66 are shown. Plot 66B shows a motion-corrected contact quality force-equivalent, for reference. Optionally, a dielectric contact quality scale is reported as the instantaneous contact quality. Additionally or alternatively, in some embodiments, dielectric contact quality is corrected for motion, for example, by time averaging, filtering, or another signal processing method.

Moreover, in some embodiments, a scale of dielectric contact quality optionally takes physiological motions into account as being themselves indicative of contact quality. In the example shown, large changes occur within the range of acceptable contact, while changes are smaller as contact is initiated, and/or as contact becomes excessive. It is to be understood, however, that the actual relationship between impedance swings and contact quality may be different, according to what is observed in calibrating a scale of dielectric contact quality for a particular probe, tissue, and/or procedure.

Figures 1D, 1E:
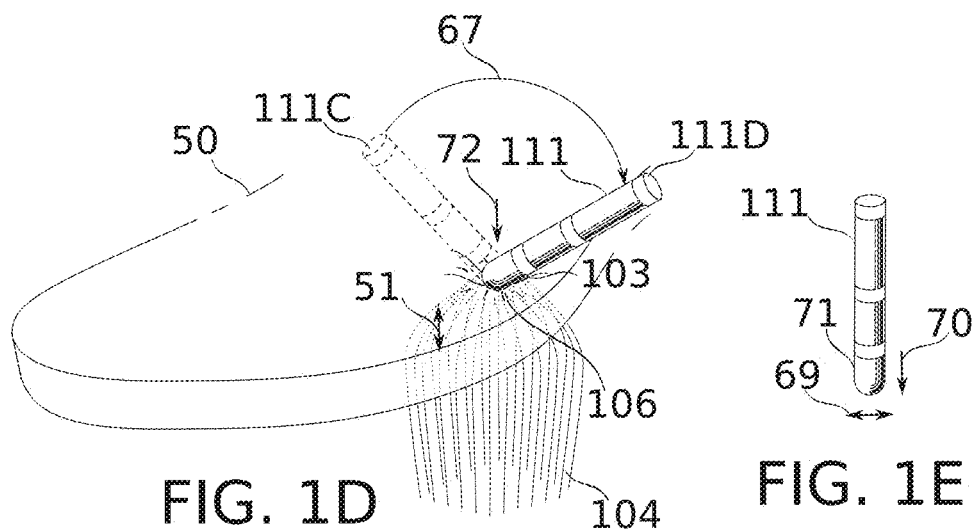
FIG. 1D schematically represents rotation of a catheter probe through a range of contact angles with a tissue wall for measurement of a dielectric contact quality therebetween, according to some embodiments of the present disclosure.
FIG. 1E schematically represents a catheter probe comprising a contact force sensor, according to some embodiments of the present disclosure.

Reference is now made to FIG. 1D, which schematically represents rotation of a catheter probe 111 through a range of contact angles 67 with a tissue wall 50 for measurement of a dielectric contact quality therebetween, according to some embodiments of the present disclosure. Reference is also made to FIG. 1E, which schematically represents a catheter probe 111 comprising a contact force sensor 71, according to some embodiments of the present disclosure.

In some embodiments, contact of probe 111 with a tissue contact region 106 comprises contact at an electrode 103 which is shaped (for example, rounded) to present a substantially similar contact geometry through a wide range of contact angles 67 as it moves between a first position 111C and a second position 111D. For a given resulting force applied by probe 111 in a direction orthogonal to tissue wall 50, it can be understood that the resulting contact surface area (and so, to a close approximation, the contact quality of that contact) should be the same in all positions. However, the determination of the forces experienced by the probe along these directions is potentially prone to error from a single-direction contact force sensor 71. If force sensor 71 is aligned to sense force along direction 70, for example, then it will potentially only sense the component of contact force 72 which is aligned with direction 70. At least a portion of the component of contact force 72 aligned with direction 69 is potentially unobserved, leading to contact angle dependence for force sensed by contact force sensor 71. Addition of one or more additional sensors (for example, to sense lateral forces) can raise engineering difficulties, since the catheter probe 111 itself is likely to be highly constrained in diameter (leaving little room for extra wiring, or even for the extra sensor itself).

In some embodiments, dielectric contact quality estimation is substantially constant (for example, constant within about 5%, 10%, 15%, or another smaller or intermediate value) while contact angle 67 is within 30° of a central angle of contact; for example, a central angle of contact comprising orthogonal positioning of probe 111 to tissue wall 50. Optionally, the angular range of substantially constant dielectric contact quality estimation is within 45°, 60°, 75°, or another larger, smaller, or intermediate angle from the central angle of contact.

Figure 1F:
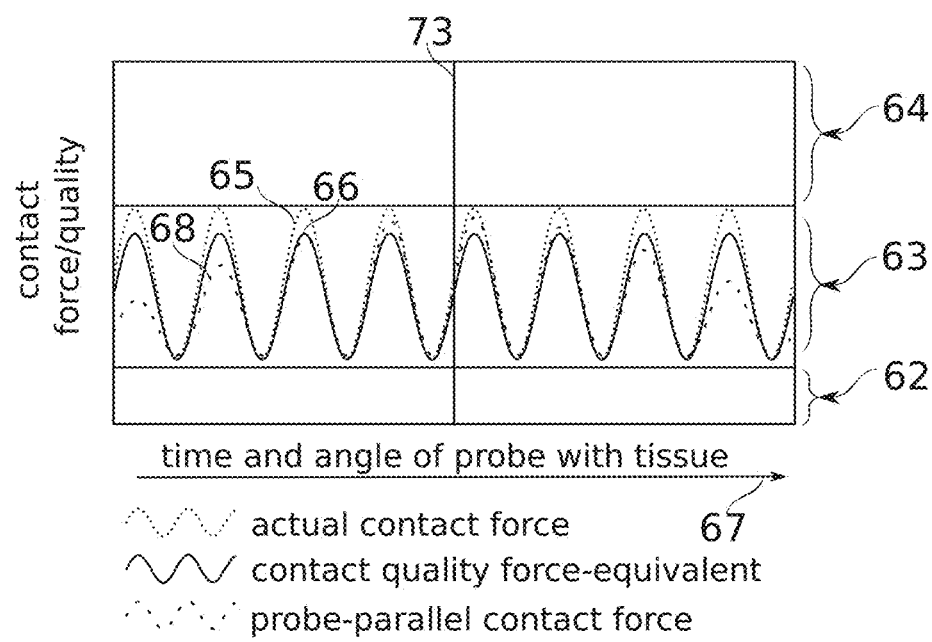
FIG. 1F is a simplified and schematic plot of contact force and dielectric contact quality as a function of time and angle of probe against a cyclically moving tissue wall, according to some embodiments of the present disclosure.

Reference is now made to FIG. 1F, which is a simplified and schematic plot of contact force and dielectric contact quality as a function of time and angle of probe 111 against a cyclically moving tissue wall 50, according to some embodiments of the present disclosure.

Contact force/quality traces 65, 66, and 68 are shown as a function of time and angle of probe with a tissue contact region 106, the angle changing in the direction of arrow 67 (shown as an arc in FIG. 1D). Cyclical motion of tissue wall 50 is also included in the traces. Trace 65 represents an actual contact force orthogonal to tissue wall 50, while trace 68 represents a contact force estimated from a contact force sensor 71 aligned to sense force exerted along the longitudinal extent of probe 111. As shown in the example, the sensed force increasing underestimates the true force as the contact angle deviates from true vertical, indicated by mark 73.

A potential advantage of dielectric contact quality measurement, in some embodiments, is that the resulting scale (measurements shown as dielectric contact quality trace 66) is optionally independent of contact angle. Optionally, this is a natural consequence of the measurement, particularly if the geometry of the contact surface is what dominates the impedance measurements. Additionally or alternatively, even if impedance itself has some angular dependence for a particular electrode configuration, the scale by which it is converted to a measure of dielectric contact quality may be calibrated to compensate. This option arises, for example, if there are one or more parameters of the multi-parameter impedance measurement which sufficiently correlate with contact angle.

System for Measurement of Dielectric Properties

Figure 1G:
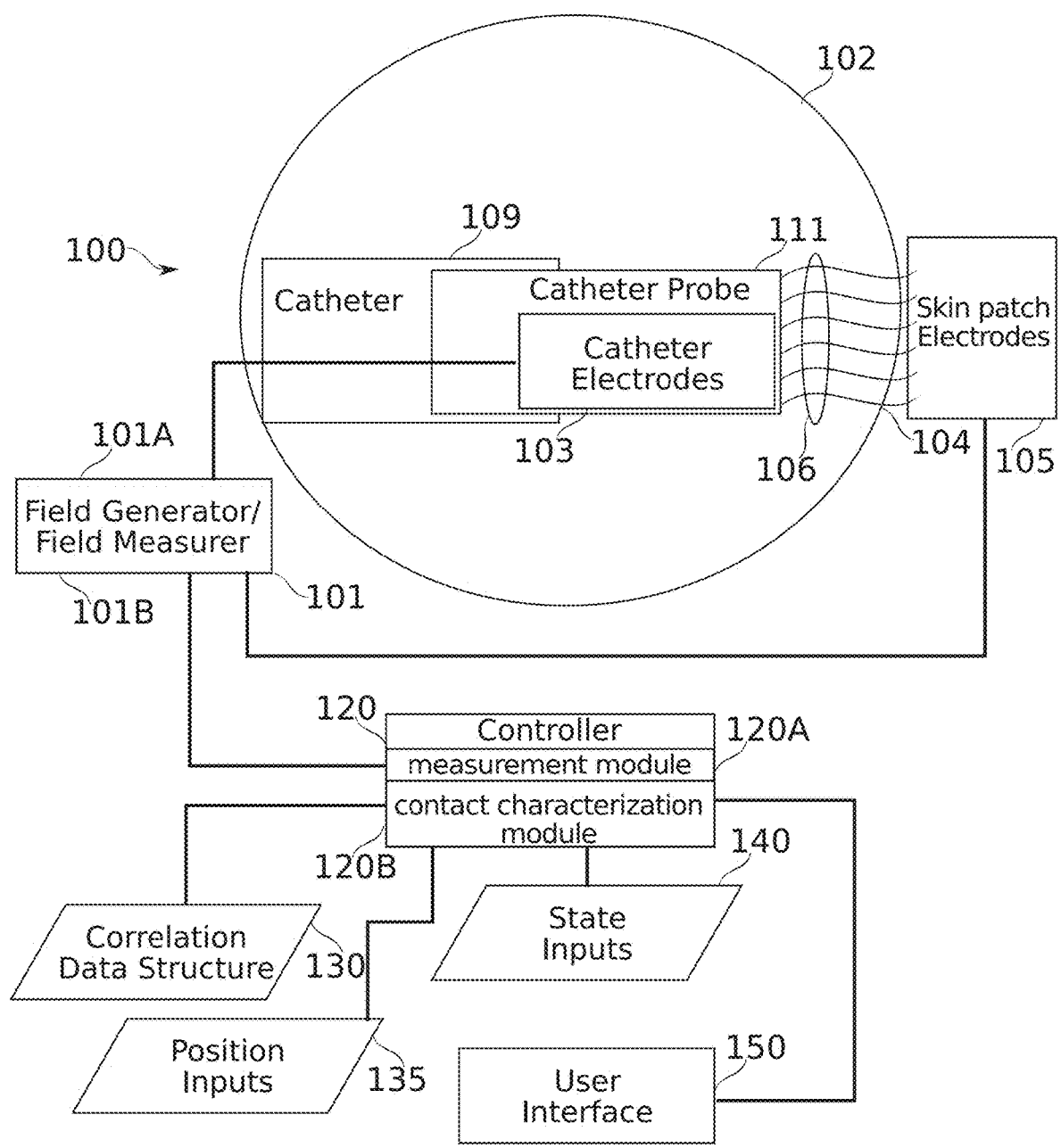
FIG. 1G schematically illustrates a system for the measurement of tissue dielectric properties, according to some embodiments of the present disclosure.

Reference is now made to FIG. 1G, which schematically illustrates a system 100 for the measurement of tissue dielectric properties, according to some exemplary embodiments of the present disclosure.

In some embodiments, dielectric properties of tissue are assessed for determining a quality of contact (dielectric contact quality) between an electrode and tissue. Optionally, the dielectric contact quality is used, for example, in the planning and/or creation of tissue lesions. In some embodiments, tissue lesions are made for treatment, for example, of atrial fibrillation, hypertrophic obstructive cardiomyopathy, neuromodulation, and/or tumors. Dielectric property measurements are made, for example, based on the frequency- and/or time-dependent response characteristics of an electrical circuit comprising a target tissue. In some embodiments, circuit response characteristics comprise output signals (e.g. changes in voltage potential) in response to one or more input signals (e.g., driving frequencies).

In some embodiments, system 100 comprises an electrical field measurement device 101B, connected to a set of catheter electrodes 103, and a set of skin-patch electrodes 105 to measure properties (for example, voltage potential and how it changes) of time-varying electrical field 104 therebetween. In some embodiments, electrical field measurement device 101B comprises a power meter (e.g., an RF power meter), a volt meter, and/or an ampere meter, configured to measure power, voltage, and/or current sensed by catheter electrode 103. The measured electrical field is generated by a field generator 101A; optionally included together in a combined electrical field generation/measurement device 101. In some embodiments, a catheter probe 111 comprising the catheter electrodes 103 is introduced to the region of a tissue to be ablated by means of a catheter 109. In some embodiments, the skin patch electrodes 105 are externally applied, for example, to the body of a patient. In operation of system 100, field 104 is induced in tissue 102 (for example, tissue of a patient's body) separating the catheter electrodes 103 and the skin patch electrodes 105. Optionally, the electrical field also extends through a target tissue region 106. Optionally, dielectric contact quality with target region 106 is assessed as part of guiding treatment administered through probe 111, for example, treatment by ablation (lesion formation).

Figure 2:
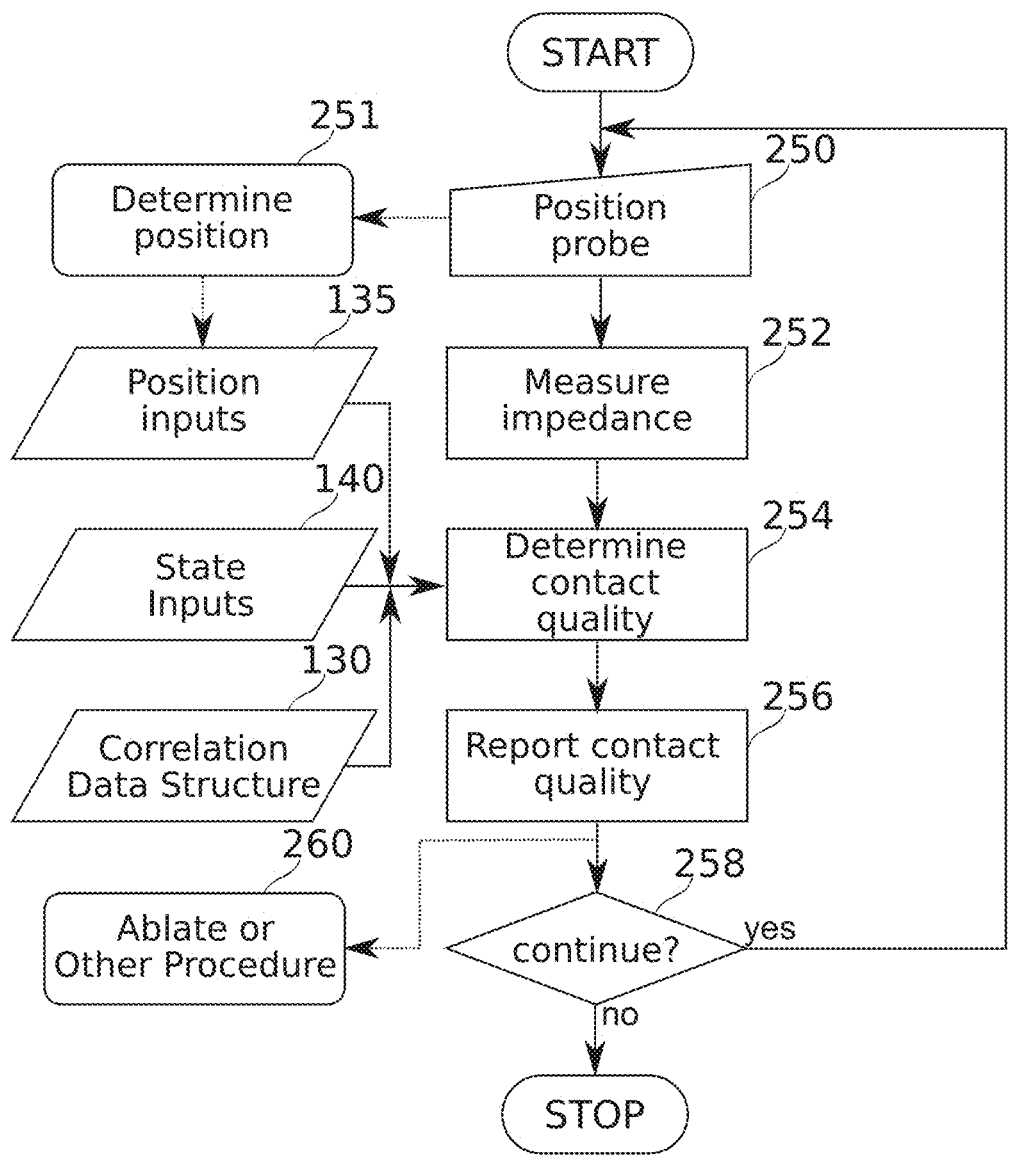
FIG. 2 is a flowchart of a method for the measurement of tissue dielectric properties for determination of contact quality, according to some embodiments of the present disclosure.

As described, for example, in relation to FIG. 2, measurements of frequency-dependent impedance in the electrical circuit(s) resulting from this configuration reflect electrical properties of tissue through which the electrical field extends (in particular, dielectric properties). The dielectric properties sensed change according to the environment of electrode 103, and in particular, according to a degree of contact with target region 106.

Optionally, the number of catheter electrodes is 2, 3, or 4 electrodes. Optionally, a greater or lesser number of catheter electrodes is used. Optionally, the number of skin patch electrodes is 4, 5, or 6 electrodes. Optionally, a greater or lesser number of skin patch electrodes is used.

Optionally, the characteristics of the time-varying electrical field 104 are chosen to be appropriate to a measurement function which is to be performed. Typically (for measurement functions), the frequencies of the electrical field used are in the range of 10 kHz to 13 kHz. In some embodiments, the frequencies of the electrical field used for measurement are in a range, for example, of about 8 kHz-15 kHz, 5 kHz-20 kHz, 10 kHz-25 kHz, or another range having the same, larger, smaller, and/or intermediate bounds.

Optionally, the number of frequencies used is 10 or fewer frequencies. Optionally, the frequencies are distributed evenly throughout the full range of frequencies chosen. Optionally, frequencies chosen are concentrated in some particular frequency range. Applied voltages are preferably in the safe range for use in humans, for example, 100-500 millivolts, and/or a current of 1 milliamp or less (a typical body resistance is about 100Ω). Resulting field strengths are in the range, for example of a few millivolts per centimeter; for example, 5 mV/cm, 10 mV/cm, 20 mV/cm, or another larger, smaller, or intermediate value. Based on requirements for data acquisition, sensing time is optionally about 10 msec per measurement (or a longer or shorter period, for example, about 100 msec, or 1 second), for embodiments including fast automated switching of frequencies and/or electrode pairs.

In some embodiments, a method of correlation (for example, as described in relation to calibrating the device of FIG. 1A, herein) is optionally used to relate measured electrical properties (dielectric-related properties in particular) of tissue as a function of a degree of contact therewith to procedure results (e.g., lesioning effectiveness), and/or to another measure of contact quality such as contact force. It can be understood that any sufficiently dense sampling of frequencies may be initially measured with respect to a particular system and set of tissue conditions to determine which frequencies show the most useful results. The reduction to a number practical for online use can be based on which frequencies yield data having the greatest statistical correlation with results. It has been found by the inventors that ten or fewer frequencies, distributed, for example, within the range of 10 kHz to 13 kHz, are useful to allow contact assessment. It should be noted that published permittivity and conductivity values of many tissues, including heart, are roughly linear in log: log plots over ranges of a few hundred kHz within the range mentioned, which potentially allows distinctions among tissue types to be made without a requirement for dense frequency sampling.

In some embodiments, catheter probe 111 is optionally used for ablation by RF ablation energies delivered through the catheter electrodes 103 which are also used for measurements. Optionally, catheter electrodes 103 are provided as part of a standard catheter probe, operated with a system capable of driving, sensing and/or analyzing circuits so as to acquire data suitable for dielectric property analysis.

In some embodiments, other electrodes, another catheter probe and/or another ablation method is used, for example, cryoablation, ultrasound ablation, laser ablation, electroporating ablation, or another form of ablation.

In some embodiments, the electrical field generation and/or electrical field measurement device 101A, 101B is under the control of controller 120, which itself is optionally under user control through user interface 150. Controller 120 optionally comprises a computer with CPU or other digital hardware operating according to programmed code. Controller 120 is described herein as a multi-functional module; however, it is to be understood that functions of controller 120 are optionally distributed among two or more modules of the system.

Electrical field generation by device 101; for example, to probe dielectric properties of the tissue environment by means of impedance measurements, is under the control of controller 120. Measurements from device 101, for example, of impedance parameters used in measuring dielectric properties, are communicated back to the controller 120, and/or a measurement module 120A. In some embodiments, controller 120 also comprises an ablation controller (not shown). Ablation is optionally via electrical fields (e.g., RF electrical fields) generated by device 101, or by another ablation method, for example as described herein.

In some embodiments, controller 120 comprises contact characterization module 120B, relating measurements to one or more additional parameters to produce a measure of dielectric contact quality. For example, state inputs provided at 140 optionally comprise any state relevant to the measurements, including, for example, details of the anatomy of tissue 102 and/or target region 106. Optionally, position inputs 135 are provided to define position(s) of catheter electrode 103 and/or skin patch electrodes 105 relative to anatomy.

In some embodiments, details of anatomy comprise image data giving tissue types in positions through which field 104 is induced. Optionally, details of anatomy comprise a dielectric property model of the anatomy, for example, dielectric properties inferred from image data and/or typical dielectric properties of different tissue types. Optionally, the model is refined by additional data received by electrode sensing, for example, sensing from catheter electrodes 103 and skin patch electrodes 105. In some embodiments, user interface 150 is provided with means for governing how controller 120 uses available state inputs 140 and/or position inputs 135—for example, to review and/or correct data-to-model registration, adjust model parameters, and the like.

Optionally, system 100 comprises correlation data structure 130, functionally connected with controller 120. In some embodiments, the correlation data structure comprises data by which measured electrical field properties (in particular, those associated with dielectric properties of target tissue) are linked to dielectric contact quality. The linkage is optionally (for example) by statistical correlation, by use of a machine learning result, and/or by use of equations fit to correlation data. In some embodiments, correlations are supplemented by modeling of the effects of one or more physical properties: for example, temperature, and/or time-varying filling with fluid (such as blood) and/or gas (such as air). In some embodiments, the data structure is compiled by the application of one or more of such linkage methods to previously recorded calibration data. For example, calibration lesions are formed, and separate measurement of dielectric properties and corresponding lesion sizes (and/or other lesion state information, such as lesion type and/or condition) are performed. In some embodiments, contact force is measured along with measurements for dielectric contact quality, and correlation data structure 130 is built based on correlations between these two measures. Optionally, additional data, for example, state data such as is provided by state inputs 140, is also measured.

In some embodiments, the relationships among measurements are stored in correlation data structure 130 in such a way that a vector of dielectric properties from field generator/measurement device 101, optionally supplemented by information from state inputs 140, can be used to estimate dielectric contact quality (optionally, contact quality expressed as contact force). In some embodiments, correlation data structure 130 also comprises information relating to other tissue properties, for example, properties of an existing, targeted, or developing lesion. Lesion properties include, for example, lesion size (e.g., lesion depth, width, and/or volume), and/or type or condition (e.g., reversible, irreversible, transmural, fibrotic, and/or edematous). In some embodiments, dielectric contact quality is continuously variable, for example, expressed in arbitrary units, or in force-equivalent units. In some embodiments, dielectric contact quality comprises a category assignment—for example, contact is estimated as being within one of a plurality of contact quality categories (e.g. "insufficient", "sufficient", or "excessive" with respect to one or more criteria of a procedure such as a lesioning procedure). Optionally, an impedance contact quality assessment is associated with an estimate of likelihood; for example, a standard deviation and/or a confidence level.

Measurement of Dielectric Properties

Reference is now made to FIG. 2, which is a flowchart of a method for the measurement of tissue dielectric properties for determination of contact quality, according to some exemplary embodiments of the present disclosure.

Before stepping through the blocks of FIG. 2 in detail, there is now provided a brief overview of impedance measurement. To describe a basic measurement of impedance, the following notation is used:

W—A set of frequencies.
C—A set of catheter electrodes.
P—A set of patch electrodes.

Parameters and/or values for each of the above are, for example, as described in relation to FIG. 1G.

Impedance measurements are optionally expressed as: $Z(t)=\{Z_{w,c,p}(t)|w \in W, c \in, p \in P\}$ where $Z(t)$ is the complex impedance (resistance and reactance) measured at time t and frequency w between a catheter electrode c and a patch electrode p.

Correlation information from any single electrode pair and/or frequency is generally not a sufficient basis on which to draw conclusions. It is a potential advantage to have numerous vector components (for example, measurements at multiple frequencies between multiple electrode pairs) in order to extract sufficiently strong correlations to allow dielectric contact quality assessment. Optionally, the number of catheter electrodes is 2, 3, or 4 electrodes, or a greater or lesser number of catheter electrodes. Optionally, the number of skin patch electrodes is 4, 5, or 6 electrodes, or a greater or lesser number of skin patch electrodes. Optionally, 2-10 electrical field frequencies are used, or a greater number of frequencies.

Herein, determination and application of correlations is described in terms of vectors, for convenience of presentation. It should be understood that in some embodiments, correlations are additionally or alternatively expressed in another form.

In some embodiments, multivariate nonlinear regression and/or classification analysis is used to establish correlations and/or mappings between measurements (and/or intervals of measurements obtained as a time series) and one or more of contact quality and contact force. Optionally, correlation and/or mapping is derived from use of a machine learning technique; for example: one or more implementations of decision tree learning, association rule learning, an artificial neural network, inductive logic programming, a support vector machine, cluster analysis, Bayesian networks, reinforcement learning, representation learning, similarity and metric learning, and/or another technique taken from the art of machine learning. Optionally, the choice of technique influences the storage, expression, and/or retrieval of correlation data. For example, correlations are optionally established and/or read-out by use of a machine learning paradigm expressed as an artificial neural network expressed in terms of connected nodes and connection weights. In some embodiments, determined correlations are expressed in terms of associative rules; for example, one or more functions (optionally fitted to the calibration data) and/or lookup tables.

In some embodiments, determined correlations are expressed in terms of associative rules; for example, one or more functions fitted to the calibration data. In some embodiments, correlations are expressed in terms of one or more dielectric measurement profiles. For example, occurrence of a certain degree of contact (e.g., as measured by a force sensor) is observed during calibration to correlate with one or more impedance measurements occurring within one or more corresponding ranges. These ranges are optionally established as a dielectric property profile that serves as an indication of the corresponding degree of contact when it is observed. Alternatively or additionally to calibration with reference to another measure of contact quality, impedance contact quality measurements are correlated with the effects of carrying out a procedure (such as ablation) when a certain impedance contact quality is obtained. It should be noted that this latter procedure potentially tends to conflate non-contact parameters affecting dielectric measurement into results unless calibration also accounts for at least one variable which is contact-related (even if not describing contact itself), such as a distance of electrode advance against a target tissue.

Use of multiple field measurements potentially assists in the isolation of correlations between field measurements and dielectric contact quality. For example, it can be considered that a substantially common tissue region near (and, in particular, contacting at least one of) each catheter electrode $c_i$ contributes to the impedance $Z_{w,c,p}(t)$ measured between each pair of electrodes $(c_i, (p_1, \ldots p_m))$. This common region potentially increases correlation in impedance measurements made between each of those electrode pairs. Conversely, the impedance contributions of tissue more distant from the electrode probe, separating the electrode probe and any given patch electrode $p_j$ are potentially encoded in correlations between each of the pairs $((c_1, \ldots c_n), p_j)$.

Even though the impedance interactions of the different tissues (near-catheter and far-from-catheter) are potentially non-linear in their combined effects on measurements, it can be understood based on the foregoing how contributions of local and distant tissue are potentially separable from one another based on correlation properties.

Different tissues have different dielectric properties, providing one basis on which increasing contact with a tissue can have an effect on those properties. An electrode within a heart, for example, is potentially in contact with both blood and a wall myocardial tissue to varying degrees as an impudence contact quality with the myocardial tissue changes. Published values of dielectric properties in different tissue types show that blood and cardiac muscle, for example, comprise two potentially distinguishable tissue environment components. Features of tissue and tissue environments such as blood which affect dielectric properties (e.g. components of impedance) potentially include, for example, cellular organization, fibrous organization, and/or the presence of free fluid and/or the make-up of free fluid constituents.

Referring now to FIG. 2, prior preparation of a subject is presumed to have been performed before entry into the flowchart at block 250. In some embodiments, skin patch electrodes are positioned on the body of a patient, in good electrical contact therewith. Optionally, the patch electrodes are, for example, about 5-15 cm across. Optionally, 3-5 skin patch electrodes are used, e.g., 3 electrodes.

At block 250, in some embodiments, catheter electrodes are brought into position, for example, by navigation through a catheter to a tissue region (for example, left atrium) at which lesions exist and/or are to be created. Optionally, at block 251, the position is determined (e.g., from co-ordinates provided by catheter navigation system), and converted to position inputs 135 for later use as will be described in relation to block 254.

At block 252, in some embodiments, fields of selected frequencies are applied between catheter electrodes C and skin patch electrodes P to obtain measurements of impedance. Measurements of field 104 (for example by field measurement device 101B) allow determination of a characteristic impedance at each frequency, and for each electrode selection, which produce the set of impedance measurements Z(t).

At block 254, an impedance contact quality determination is made. Determination of dielectric contact quality optionally comprises interpretation in view of a current environment (e.g., rough position in a body) of catheter electrodes C, as provided, for example, by position inputs 135 and/or state inputs 140. In some embodiments, time history of state inputs is taken into account; for example, oscillations as a function of heartbeat and/or respiration, and/or maximum/ minimum values recently recorded. Use of inputs additional to impedance measurements provides a potential advantage by constraining conditions of the measurements so that variables relating to impedance contact quality can be isolated.

In some embodiments, recorded data (comprising impedance and associated condition data) is expressed as a time series such as: $X(t)=(Z(t), A(t))$, $t=t_0, t_1, t_2, \ldots$, wherein $X(t)$ represents all measurements as a function of conditions and measurements, $Z(t)$ is the impedance component of the measurements, and $A(t)$ represents associated conditions of the impedance measurements, for example, known anatomical attributes, other prior information, or other simultaneously determined information (for example, organ type, and measurement location).

In some embodiments, $X(t)$ is related to another vector $Y(t)$ describing an assessment of contact with the tissue, based on use of calibration information in correlation data structure 130. Calibration is described, for example, in relation to FIG. 1A, herein. In some embodiments, calibration of the procedure comprises, for example, statistical analysis and/or machine learning which determines correlations between separately determined states of $Y(t)$ and $X(t)$. In operation, these correlations are used to select likely existing states described by $Y(t)$ based on observed states of $X(t)$.

At block 256, in some embodiments, dielectric contact quality is reported. Dielectric contact quality is optionally reported according to a scale which either reports $Y(t)$ directly, or is a transform of $Y(t)$. Optionally, dielectric contact quality is reported as a value in arbitrary units, and/or as a value in units which correspond to a reference scale, for example, contact force (e.g., in units of equivalent force, equivalent gram-force, or another reference-equivalent unit). Optionally, dielectric contact quality is reported as a categorizing assessment of contact quality. In some embodiments, the categories comprise:

Insufficient dielectric contact quality (for achieving the purpose at hand, for example, lesioning);

Sufficient dielectric contact quality (for the same purpose); and/or

Excessive contact quality (e.g. contact which is associated with a dangerous amount of contact force, so that there is a significant risk of perforation or other unintended damage to the contacted tissue wall).

Figure 4:
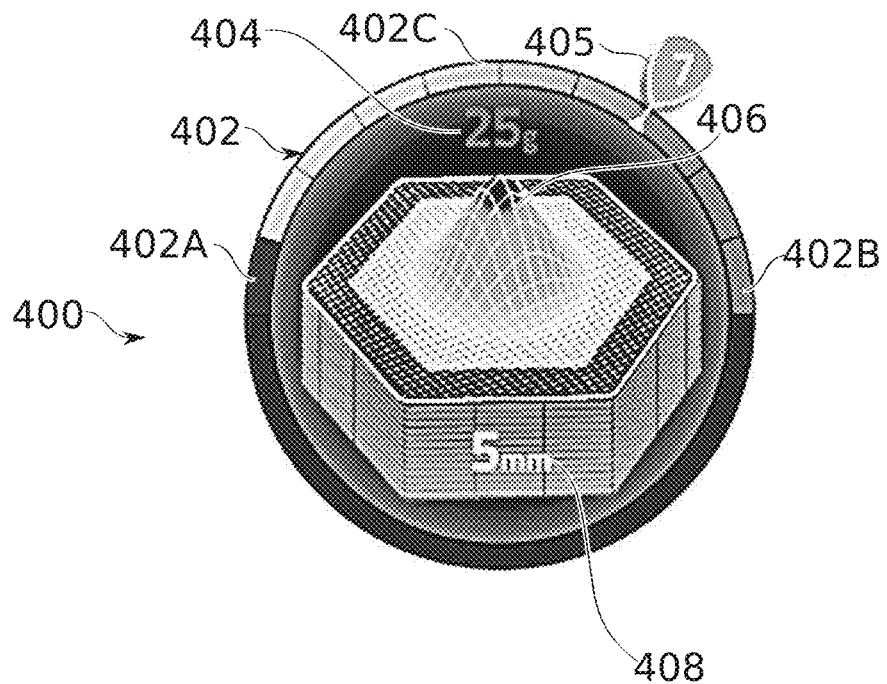
FIG. 4 illustrates a graphical user interface (GUI) widget for display of dielectric contact quality information to a user, according to some embodiments of the present disclosure.

An example of a simultaneous graphical presentation of dielectric contact quality information in categorized, arbitrary unit, and contact force-equivalent form is described herein in relation to FIG. 4.

At block 260, in some embodiments, there may be a side-branch of the contact quality assessment loop during which ablation—or another procedure to which dielectric contact quality is relevant—is optionally performed. Optionally, ablation is performed in parallel with a sequence of loops passing blocks 250-258; with additional and/or continuing ablation performed during each loop. Optionally, entry into block 260 and/or control of ablation within block 260 is at least partially dependent on a dielectric contact quality assessment. For example, initiation of ablation is optionally blocked and/or yields an alert at user interface 150 if contact quality is insufficient (additionally or alternatively, excessive) for safe and/or reliable lesioning. In some embodiments, an ongoing treatment procedure (such as an ablation) is controlled based on contact quality. For example, a power or other parameter of an ablation treatment (such as power supplied to an RF ablation probe) is optionally adjusted in coordination with variations in contact quality. Optionally, during an ablation, an ablation parameter is adjusted based on changes to contact quality. For example, ablation power is raised to compensate for lowered contact quality and/or lowered to compensate for higher contact quality (e.g., as may occur due to motions of heartbeat and/or respiration). Optionally or additionally, another ablation parameter is adjusted; for example, frequency, phase, electrode selection, signal timing, or another parameter of ablation. This provides a potential advantage for improving uniformity and/or predictability of lesioning in dynamic conditions. In some embodiments, whether or not to ablate during a particular loop is determined based, for example, on an estimate of contact quality being in and/or remaining in an acceptable range. If paused, the ablation optionally continues during a subsequent loop where appropriate conditions are restored.

For reference, it is noted that in catheterized ablation treatment of atrial fibrillation, a typical targeted time of RF ablation (for each of an optional plurality of ablation foci) is, for example, within about 10-30 seconds, 10-40 seconds, 10-60 seconds, or within another range of times having the same, higher, lower, and/or intermediate values. When heating tissue to ablate, for example by RF ablation, typical average power delivery is, for example, about 10 W, 20 W, 30 W, 35 W, or another larger, smaller, or intermediate value. Typical radio frequencies used with RF ablation are, for example, in the range of about 460-550 kHz; and commonly about 500 kHz. It is to be understood that, optionally, another ablation modality is used.

In some embodiments, treatment (ablation heating energy, for example) is delivered through the same electrode(s) as are used for measurement of impedance values reflecting dielectric contact quality with tissue, e.g., as RF energy at a frequency inducing appropriate "resistive" losses in the tissue which result in tissue heating. It is a potential benefit to ablate and measure using the same electrodes. For example, it can result in less instrumentation required, less positioning coordination required, and/or a more direct relationship between measurements made and results achieved. Additionally or alternatively, in some embodiments, measurements and ablation are performed by separate instruments (however, in this case, at least some form of mechanical coupling and/or contact between the instrument probes should be provided for so that the dielectric contact quality measurement is relevant to the effects of the treatment probe). As also mentioned hereinabove, ablation is optionally by any ablation method known.

At block 258, in some embodiments, a determination is made as to the continuation of the procedure. If the procedure continues, flow returns to block 250. Otherwise, the procedure ends.

Display of Dielectric Contact Quality

Reference is now made to FIG. 4, which illustrates a graphical user interface (GUI) widget 400 for display of dielectric contact quality information to a user, according to some exemplary embodiments of the present disclosure. Optionally, features of GUI widget 400 described hereinbelow are additionally or alternatively provided by separate displays. However, there is a potential advantage to providing a single display to allow at-a-glance status determination.

In some embodiments, a display function of user interface 150 comprises a display such as GUI widget 400. In some embodiments, GUI widget 400 comprises one or more indications of contact quality between a probe 111, 112 and a target tissue region 106. In some embodiments, one such indication comprises a dielectric contact quality scale 402. Optionally, scale 402 distinguishes a plurality of regions (e.g., regions 402A, 402B, 402C), which indicate different qualitative contact quality states. For example, scale region 402A optionally represents insufficient contact (e.g., contact ineffective for the production of a therapeutic result). Scale region 402B optionally represents excessive contact (e.g., contact which represents a potential danger of trauma such as organ perforation). Scale region 402C optionally represents a range within which contact is sufficient. In some embodiments, a scale marker 405 is provided which gives a relative quantitative assessment of contact quality. The scale is optionally in arbitrary units. Optionally, movement of scale marker 405 along the scale is continuous, or divided into unit steps.

In some embodiments of the invention, a force indication 404 is provided as part of GUI widget 400. In some embodiments, force indication 404 is provided in force-equivalent units (e.g., grams-force). A potential advantage of this display is to allow operators to perform procedures based on guidelines originally defined in terms of contact force (e.g., as measured by a probe force sensor), without a requirement to translate into another unit.

In some embodiments, one or more additional features are provided relating to dielectric assessment of tissue at a contact region. In some embodiments, dielectric measurement is also used to determine one or more parameters of the tissue itself. For example, GUI widget 400 includes a tissue thickness indication 408 (e.g., giving an estimated tissue thickness in mm); and/or a lesion depth indicator 406. Lesion depth indicator 406 optionally comprises a graphical illustration of measured and/or predicted lesion geometry. For example, the peak of the hill arising from the center of indicator 406 optionally represents the maximum depth of a tissue ablation lesion which is currently being assessed, and/or which is planned for ablation. The circumference of the hill optionally represents an estimated lesion diameter.

It should be understood that the graphical representation of these functions optionally assumes other forms; the specific graphical representations of GUI widget 400 comprise an illustrative example of how various indication functions are optionally combined.

Examples of Dielectric Contact Quality as a Predictor of Contact Force

Figure 5:
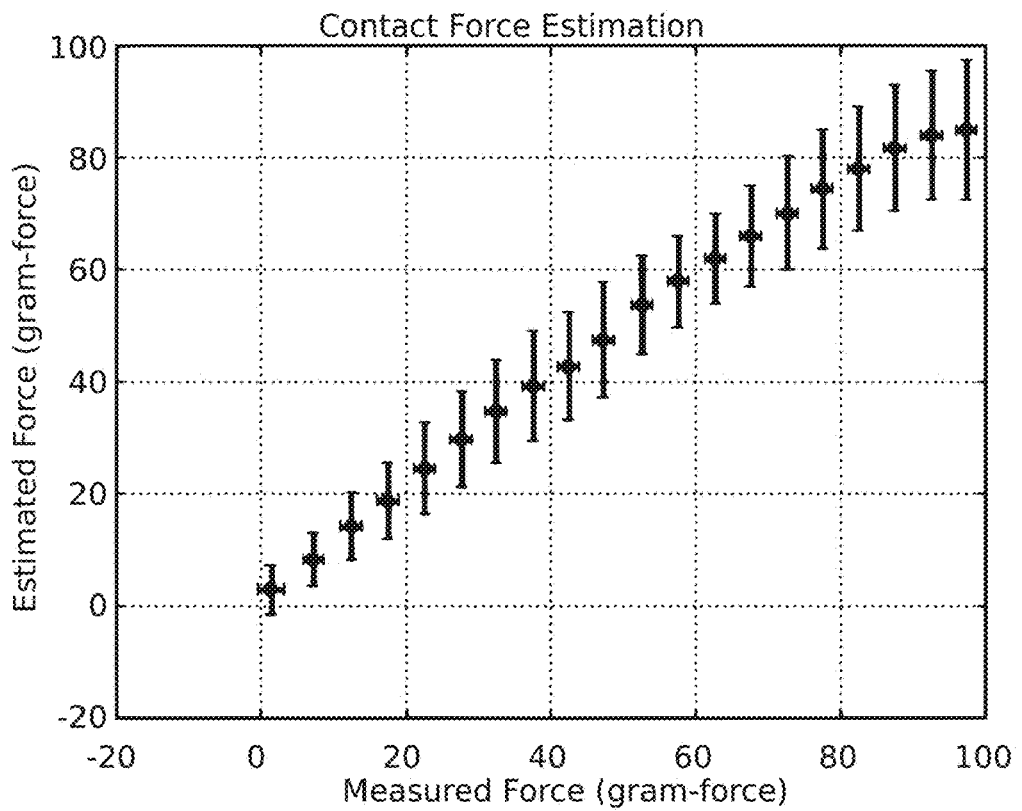
FIG. 5 is a graph presenting estimates of contact force derived from dielectric contact quality measurements, the estimated contact forces being plotted with respect to directly sensed contact forces, according to some embodiments of the present disclosure.

Reference is now made to FIG. 5, which is a graph presenting estimates of contact force derived from dielectric contact quality measurements, the estimated contact forces being plotted with respect to directly sensed contact forces, according to some embodiments of the present disclosure.

To generate data for this graph, contact force was measured by a force sensing probe pressed against an ex vivo preparation of myocardial tissue (porcine right ventricle tissue at physiological temperature). Corresponding dielectric contact quality was determined by dielectric property measurements, made for example as described in relation to FIG. 2 herein, and converted by means of a classifier to a contact force equivalent. The classifier was constructed based on a separate set of calibration measurements, for example as described in relation to FIG. 1A, herein. For all measurements, the root mean squared error (RMSE) between actually measured and estimated contact force was about 8.4 grams-force.

It can be seen from the graph that the classification results produced a strong linear trend, deviating to an underestimation (and somewhat larger error) near the top of the tested force range. This deviation potentially corresponds to less distinguishable force levels in the upper range; for example, as other parameters of contact to which dielectric contact quality is sensitive (e.g. area of contact) approach maximum values.

Figure 6:
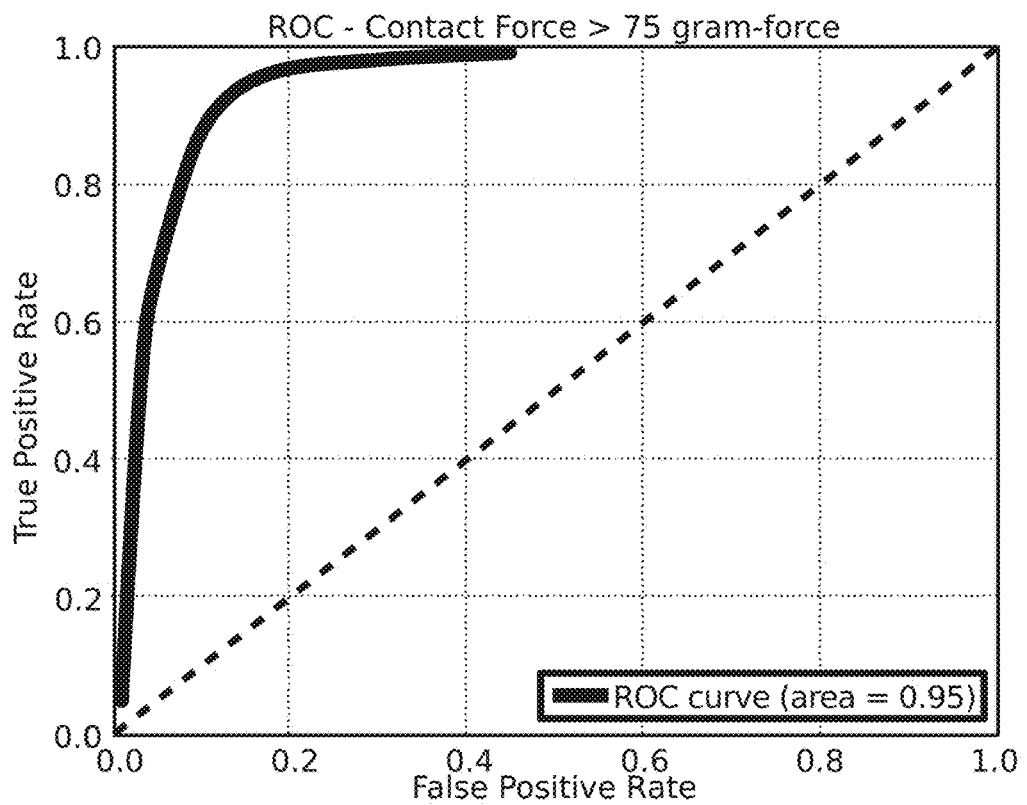
FIG. 6 is a graph of receiver operating characteristic (ROC) presenting for the data of FIG. 5 a true positive rate versus false positive rate for dielectric contact quality-based estimation of contact force above a threshold of grams-force, according to some embodiments of the present disclosure.

Reference is now made to FIG. 6, which is a graph of receiver operating characteristic (ROC) presenting for the data of FIG. 5 a true positive rate versus false positive rate for dielectric contact quality-based estimation of contact force above a threshold of 75 grams-force, according to some embodiments of the present disclosure. It should be understood that each point along the ROC graph corresponds to different multiparameter dielectric readings which have been mapped to the estimated contact force on which the ROC graph is based.

On an ROC graph, true positive rate corresponds to sensitivity (Y axis; higher is more sensitive), and false positive rate corresponds to 1-specificity (X axis; further left is more specific). Perfect classification (100% sensitivity and specificity) would appear as a point in the upper left corner of the graph; the diagonal line is the line of no classification (chance). For the 75 grams-force threshold, the graph shows an area under the ROC curve of about 95% of the total graph area. This fairly high value appears to corroborate conclusions described above with respect to FIG. 5.

Figure 10:
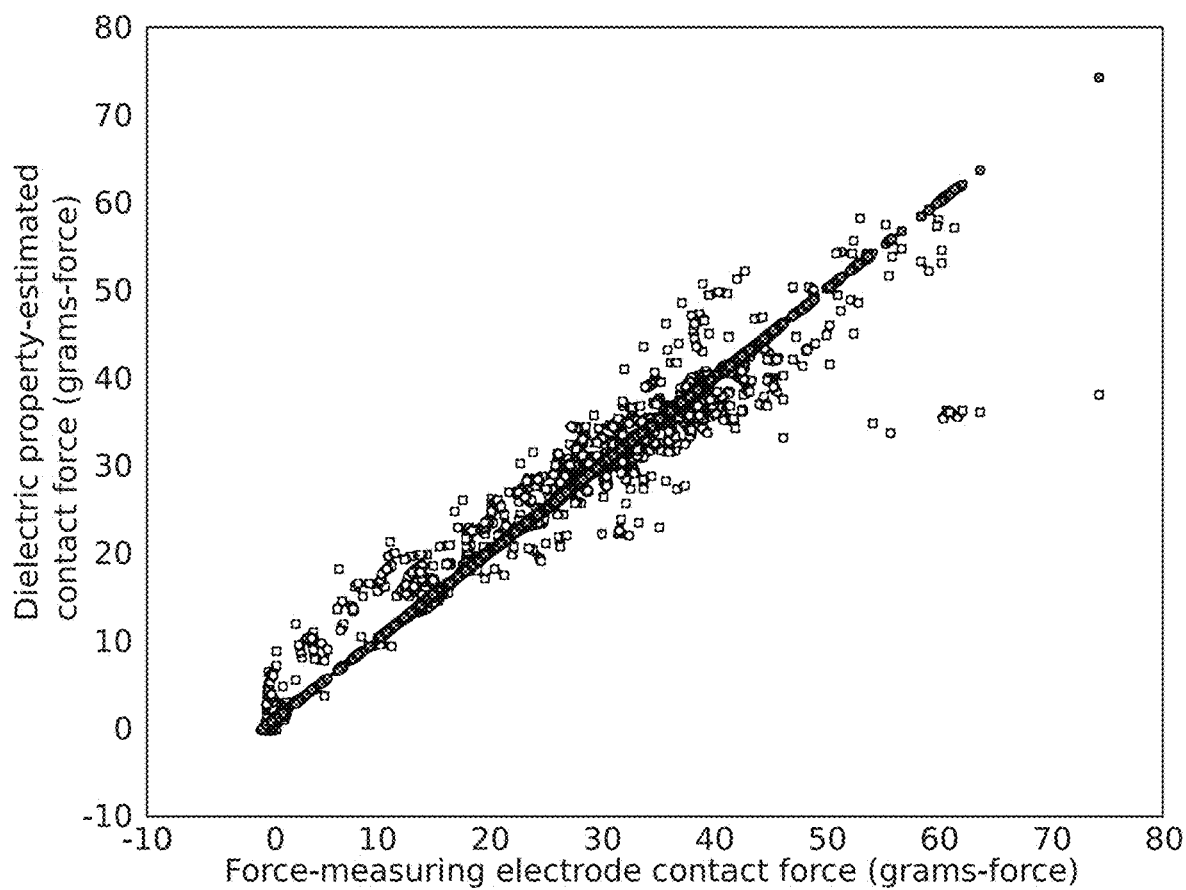
FIG. 10 is a graph presenting dielectric property-estimated contact force vs. directly measured force, according to some exemplary embodiments of the invention.

Reference is now made to FIG. 10, which is a graph presenting dielectric property-estimated contact force vs. directly measured force, according to some exemplary embodiments of the invention.

On the vertical axis, values represent the returned contact force estimate (in grams-force) of a contact force estimator operating on dielectric measurements. On the horizontal axis, values represent grams-force measured by a TactiCath™ catheter probe from St Jude Medical (legacy Endosense system). Measurements were made with respect to contact with porcine left atrium wall. Open (white centered) plot points represent corresponding data points (measurements made through the same catheter, either dielectrically or via the force sensor). Darkened (gray-centered) plot points represent the unity line of the direct force measurements plotted against themselves.

Figure 11A:
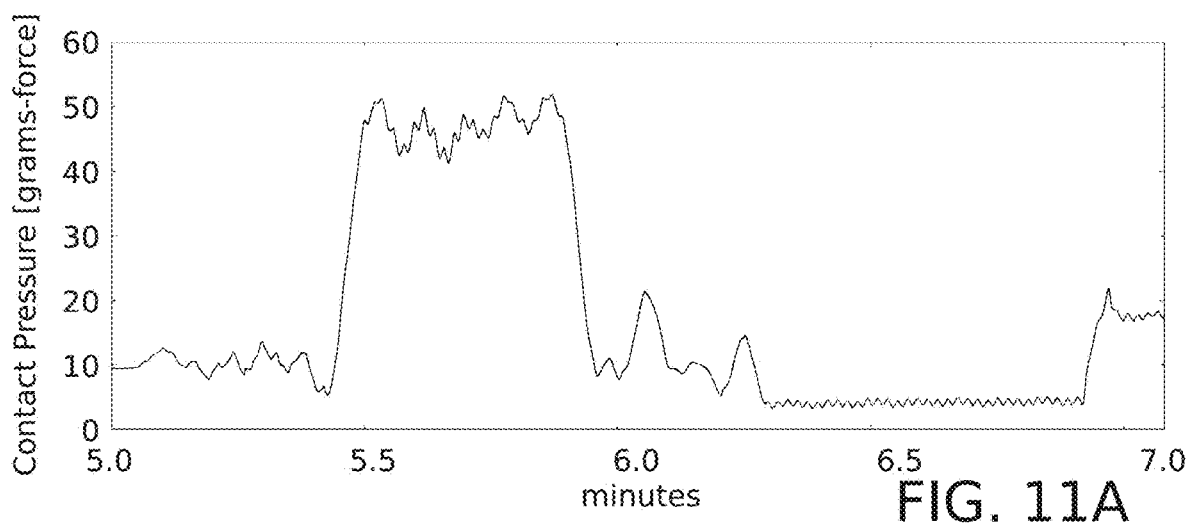
FIG. 11A graphs contact force measurements using a force sensing catheter.
Figure 11B:
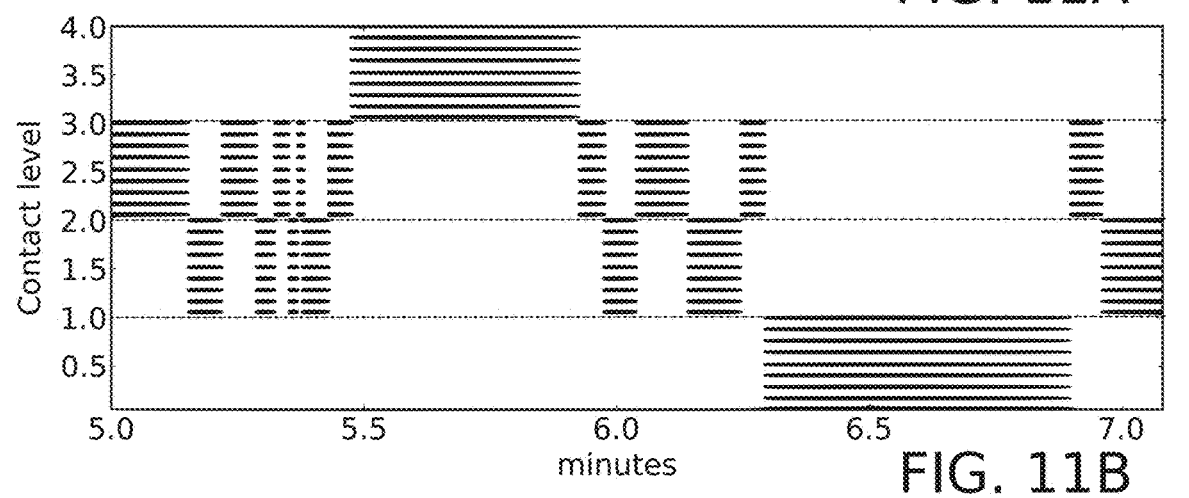
FIG. 11B graphs contact quality level estimates made based on dielectric measurements for the epoch also shown in FIG. 11A.
Figure 11C:
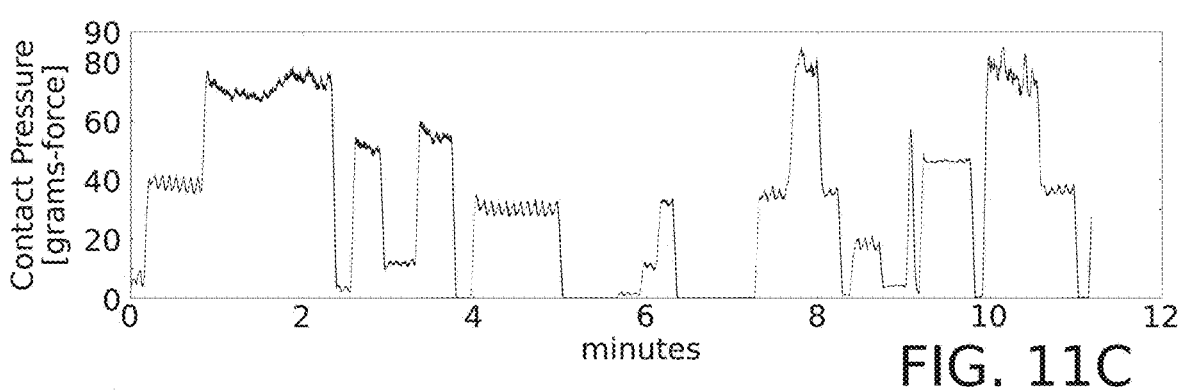
FIG. 11C graphs contact force measurements using a force sensing catheter.
Figure 11D:
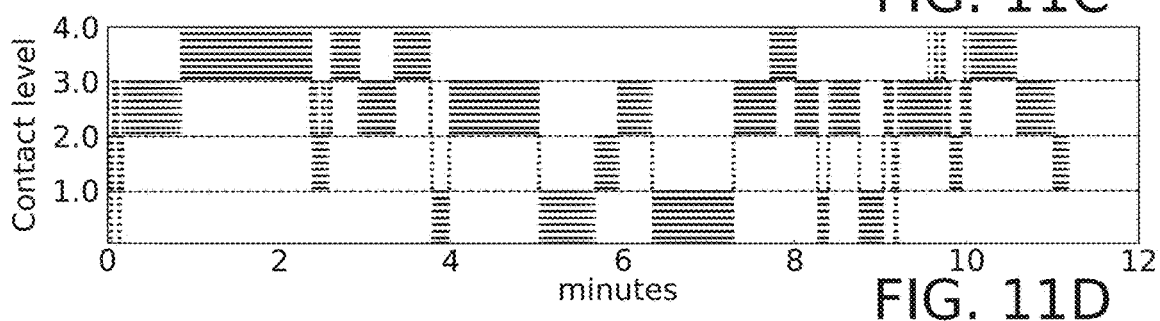
FIG. 11D graphs contact quality level estimates made based on dielectric measurements for the epoch also shown in FIG. 11C.

Reference is now made to FIGS. 11A and 11C, which graph contact force measurements using a TactiCath™ catheter (as described in relation to FIG. 10). Reference is also made to FIGS. 11B and 11D, which graph contact quality level estimates made based on dielectric measurements (also as described in relation to FIG. 10). The epochs in minutes of FIGS. 11A-11B correspond to one another; as is also the case for FIGS. 11C-11D. In FIGS. 11B and 11D, the contact levels are set between 0 and 1.0 for estimated contact forces below 10 grams-force; between 1.0 and 2.0 for estimated contact forces between 10 and 25 grams-force; between 2.0 and 3.0 for estimated contact forces between 25 grams-force and 40 grams-force, and between 3.0 and 4.0 for estimated contact forces above 40 grams-force.

Reference is now made to TABLE 1, which displays in tabular form data from the experiments outlined in FIGS. 10-11D. The data from both measurement types (directly measured contact force and estimated contact quality) have been converted to force levels of low, optimal, high and exceed, which use the same respective thresholds (<10 grams-force, 10-25 grams-force, 25-40 grams-force, and >40 grams-force) as are also shown in FIGS. 11B and 11D. It should be noted that the estimated contact quality categorization may be considered "safe" with respect to values in the "exceed" category (the category of potentially unsafe levels of contact force), since the estimator makes the "exceed" categorization at the same level of contact, or a lower level of contact, than the categorization based on the measured contact force.

TABLE 1

|  |  | MEASURED CONTACT FORCE CATEGORY | | | |
|---|---|---|---|---|---|
|  |  | Low | Optimal | High | Exceed |
| ESTIMATED CONTACT | Low | 87% | 3% |  |  |
|  | Optimal | 13% | 85% | 10% |  |

TABLE 1-continued

|  |  | MEASURED CONTACT FORCE CATEGORY | | | |
|---|---|---|---|---|---|
|  |  | Low | Optimal | High | Exceed |
| QUALITY CATEGORY | High | | 12% | 85% | 12% |
|  | Exceed | | | 5% | 88% |

3-D GUI Widget for Organ View Orientation

Figure 7A:
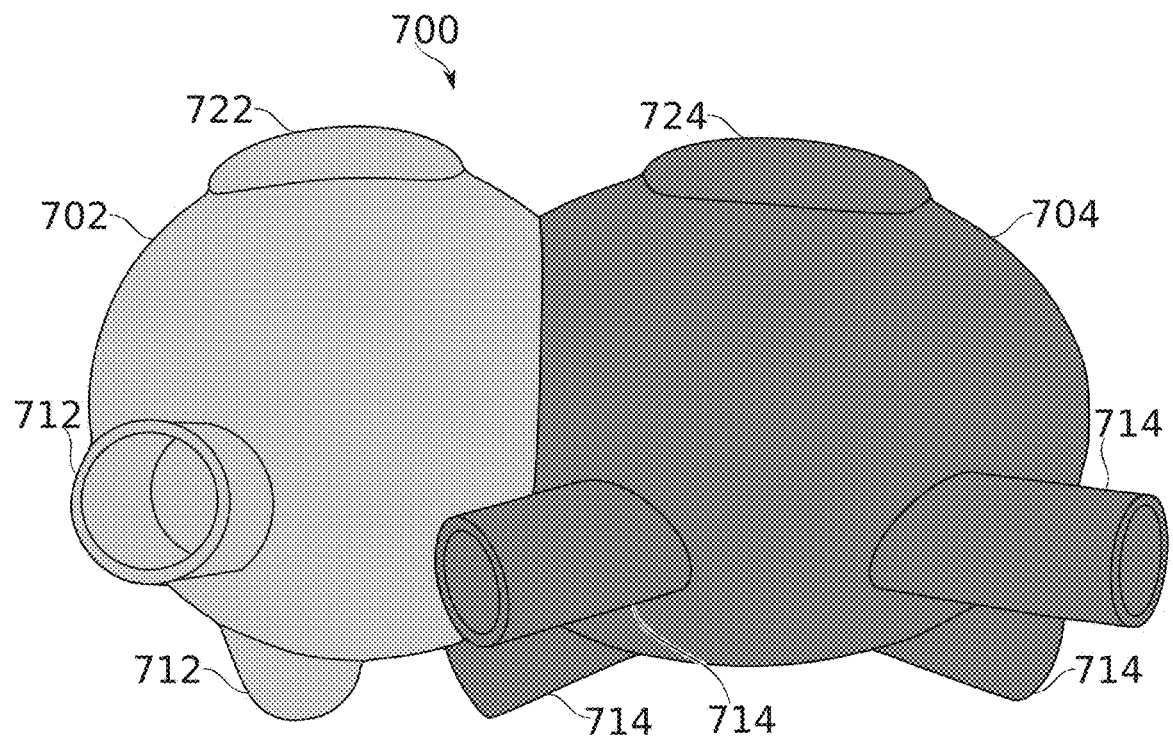
FIG. 7A schematically illustrates a view of a graphical user interface (GUI) widget, representative of the-D orientation of the atria of a heart in space, according to some embodiments of the present disclosure.
Figure 7B:
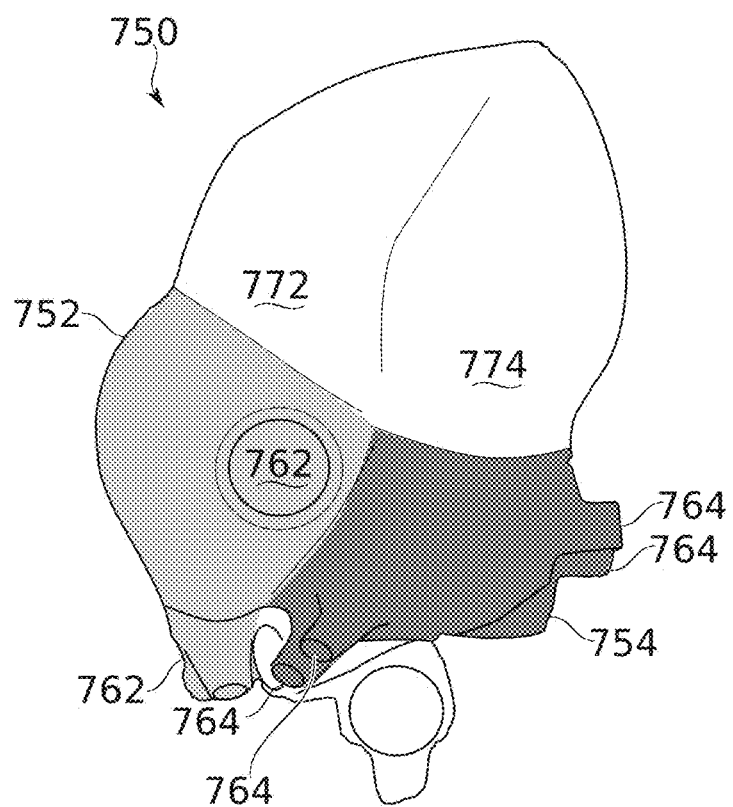
FIG. 7B schematically illustrates a heart in an orientation corresponding to the orientation of GUI widget, according to some embodiments of the present disclosure.

Reference is now made to FIG. 7A, which schematically illustrates a view of a graphical user interface (GUI) widget 700, representative of the 3-D orientation of the atria of a heart in space, according to some embodiments of the present disclosure. Reference is also made to FIG. 7B, which schematically illustrates a heart 750 in an orientation corresponding to the orientation of GUI widget 700, according to some exemplary embodiments of the present disclosure.

In some embodiments, a GUI widget 700 comprises a schematic graphical representation of an anatomical structure; for example, at least a portion of a heart 750. The schematic graphical representation is optionally implemented, for example, as a 3-D model and/or as a set of 2-D icons representing views of the anatomical structure in different orientations. In some embodiments, the widget 700 comprises a dynamic icon, changing appearance according to a virtual orientation of the schematic graphical representation. In some embodiments, the schematic graphical representation includes one or more reference bodies (for example, atrial representations 702, 704); distinguishable in their orientation by their spatial relationships to each other, and/or by one or more indicating features (e.g. vascular segments 712 and 714, and/or valve indicators 722 and 724). Optionally, the indicating features protrude from the reference bodies 702, 704. In this and following examples, shading is also used as a distinction, with the right atrium 752 or its right atrial representation 702 (and associated features) being shaded in light gray, and the left atrium 754 or its left atrial representation 704 (and associated features) being shaded in dark gray. Optionally, color, texture, or another aspect of visual appearance is used to help emphasize distinctions. For example, the left atrium is optionally colored red and/or orange, and the right atrium blue and/or green.

Optionally, atrial representation 702 corresponds to right atrium 752 of a heart 750, atrial chamber representation 704 corresponds to left atrium 754 of a heart 750, vascular segments 712 correspond to right atrium connected segments of the superior and/or inferior vena cava 762, vascular segments 714 correspond to left atrium connected segments of the pulmonary veins 764, valve indicator 722 corresponds to the tricuspid valve leading from the right atrium 752 to right ventricle 772, and/or valve indicator 724 corresponds to a mitral valve leading from left atrium 754 into left ventricle 774.

In some embodiments, GUI widget 700 is provided as a reference for assisting determination of the orientation of a corresponding view of a heart 750. For example, GUI widget 700 is displayed on a screen alongside a view of heart 750, in a 3-D orientation suitably corresponding to the displayed 3-D orientation of heart 750.

Optionally, widget 700 is linked to GUI inputs so that it also acts as an orientation control. For example, event handling software connected with GUI widget 700 is configured to receive click, drag, touch, swipe, and/or any other suitable user input gesture directed to (e.g., on, alongside, and/or passing over) the displayed GUI widget 700. Optionally, the event handling software in turn induces rotation of the displayed view of GUI widget 700 and an associated view of heart 750 in synchrony, based on the user input gestures. Optionally, events are interpreted as simulating physical interaction; for example, simulating rotation as if motion gestures are contacting the displayed surface of the GUI widget and causing it to rotate in the gesture direction. Optionally, the event handling software defines hotspots for selection of particular views. For example, clicking on (or otherwise indicating) a particular region of GUI widget 700 optionally triggers re-orientation of that region to face the operator. Additionally or alternatively, indicating a particular region alongside GUI widget 700 triggers a rotational step (for example a change in orientation of 90°). In some embodiments, rotation of GUI widget 700 is triggered by input events to other controls/display elements; for example, gestures which simulate direct manipulation of a view of the heart 750, inputs to sliders, automatic view changes in response to navigation movements of a catheter probe, etc. It should be understood that the input and handling examples provided are non-exhaustive, and not limiting of the scope of the concept.

In some embodiments, GUI widget 700 is used to assist in manipulating and/or comprehending an anatomically correct view of a heart 750, optionally in conjunction with the positioning and orientation of treatment tools, such as catheter probes. Even though the physician is well familiar with the anatomy of an organ targeted for treatment, computer-visualized surgery can present a very wide range of views which may themselves create opportunities for confusion. For example, anatomical views are optionally presented as solid, transparent, partially transparent, and/or cutaway images; each of which obscures or reveals anatomical landmarks in different ways. Additionally or alternatively, views can be presented at different scales: for example, whole-organ displays, and/or magnified views of an organ in the vicinity of a region targeted for treatment. Magnified views in particular are prone to creating confusion over position and/or orientation, since key landmarks providing visual context may be out of the frame of view. Optionally, color data is superimposed on anatomical shape data, for example, to indicate tissue health, thickness, and/or another feature. Some organs, and in particular the heart, are in constant motion, which movement in a view display optionally reflects. Moreover, structures surrounding and/or connecting to an organ (particularly in the case of the multiply connected heart) are optionally represented visually to variable extents of completeness from case to case, and/or application to application, which can also influence the appearance of a target organ in context. It is finally mentioned that an unfamiliar orientation or an unusual distortion of an organ view can itself give rise to uncertainty. For example, the orientation of the heart in FIG. 7B (corresponding also to view 791 of FIG. 7D) is not as usually shown in anatomical textbooks, but rather shown as seen from beneath, with ventral side up, and dorsal side down. View 796 of FIG. 7D is also unusual, being an upside-down dorsal view of a heart 750.

Optionally, features selected to help mark orientation of GUI widget 700 correspond to (without necessarily anatomically duplicating in detail) anatomical features which a physician is likely to be concerned with during treatment. Potentially, this helps to reduce the "cognitive distance" between what the physician is really looking for, and what the GUI widget 700 directly represents. For example, catheter-guided treatment of atrial fibrillation by cardiac tissue ablation optionally comprises aspects such as: reaching the right atrium 752 via a branch of the vena cava 762, crossing the septal wall between atria for access to treatment locations within the left atrium 754, and ablation from within the left atrium 754 of one or more regions defined by the positions of the pulmonary veins 764. Each of these anatomical features is optionally represented by corresponding features of GUI widget 700, for example as identified hereinabove. In contrast, it is a potential advantage to suppress features which are not directly relevant to tasks of the treatment itself, even if these are anatomically and/or functionally important otherwise. For example, GUI widget 700 optionally indicates the positions of the tricuspid valve and mitral valve (by valve indicators 722 and 724, respectively), but optionally omits showing the ventricles to which they connect. It is also a potential advantage to avoid an excess of detail even in features that are represented: for example, the degree of schematic representation in FIG. 7A is such that the valves are represented only by bulges. Indeed, an alternative interpretation of valve indicators 722, 724 is as shrunken representations of the ventricles themselves.

Optionally, features of the 3-D model underlying GUI widget 700, and/or of its presentation, are provided to create a relatively consistent, rotationally distinct, appearance. Suppression of the ventricles 772, 774, for example, provides a potential advantage by reducing the tendency of the ventricles to obscure the atrial representations 702, 704 and their vascular landmarks 712, 714. Landmarks are preferably provided in sufficient density for identification at any orientation, without over-providing to the point that the landmarks become themselves distracting. Optional coding of structures by color and/or shading potentially helps to make it clear at a glance at least the general orientation of the GUI widget 700.

Optionally, GUI widget 700 is constructed using shapes and/or shape relationships suggestively corresponding with shapes of actual anatomy, even though they do not literally depict them. The shapes optionally comprise an assemblage of basic geometrical figures. Vascular structures, for example, are optionally represented as straight tubes or cylinders; chambered structures as ellipsoids; aperture structures (such as valves) as flattened ellipsoids, etc. Optionally representation as a mesh structure is used. Use of mesh model may allow closer approximation of actual heart anatomy to be achieved. However, a potential advantage of representing identified features as simple geometrical objects is that they remain easily identifiable and/or clearly distinctive from a wide range of viewpoints. Furthermore, such shapes potentially help to free the widget from irrelevant (non-differentiating) visual information.

In some embodiments, a rough size difference among features helps to create an orienting asymmetry and/or readier identifiability. Optionally, such differences are selected to evoke similar differences in the actual anatomy. For example, right atrial representation 702 is shown slightly smaller than the more oblong left atrial representation 704, while the vena cava branches 712 are shown larger than the pulmonary vein branches 714. Such correspondences with anatomical relationships are not necessarily quantitative depictions of dimension ratios. However, they potentially serve a mnemonic function, by schematically evoking salient details of the actual anatomy while requiring a minimum of cognitive load to be identified.

Figure 7C:
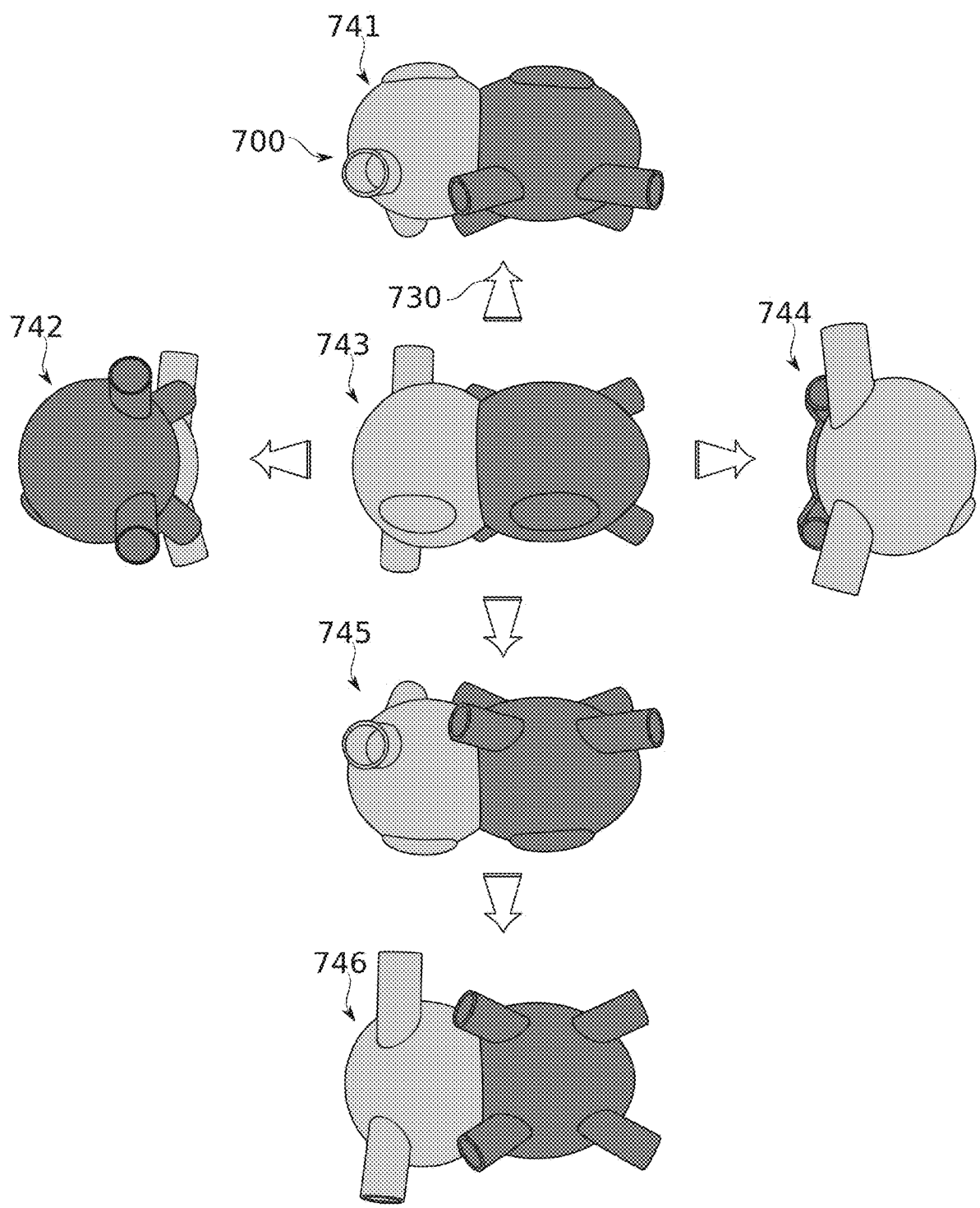
FIG. 7C shows views of six different orientations of GUI widget, separated by about ° from each other, according to some embodiments of the present disclosure.
Figure 7D:
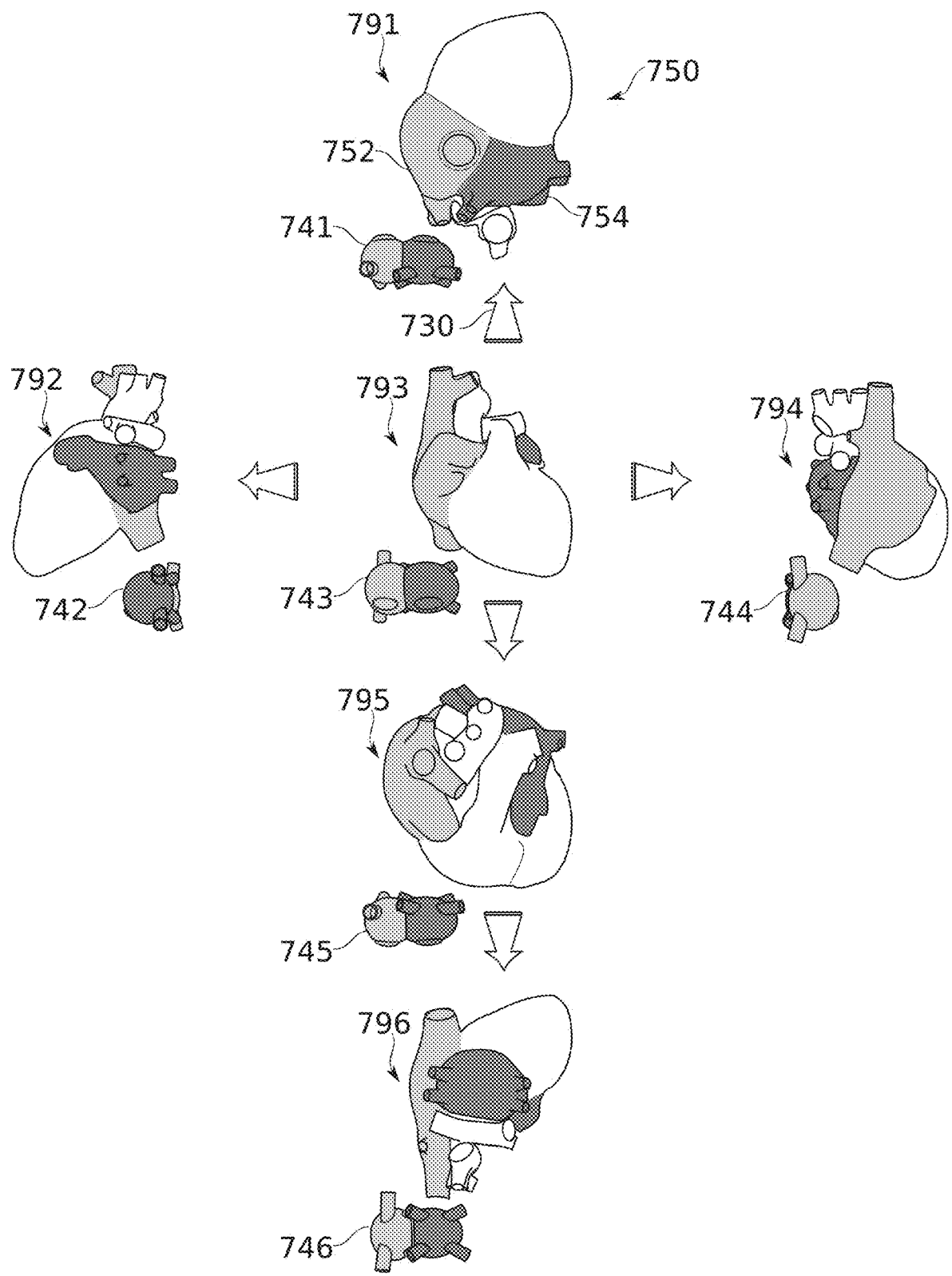
FIG. 7D shows the views of FIG. 7C reduced in size, alongside corresponding anatomical views of a heart, according to some embodiments of the present disclosure.

Reference is now made to FIG. 7C, which shows views 741, 742, 743, 744, 745, 746 of six different orientations of GUI widget 700, separated by about 90° from each other, according to some exemplary embodiments of the present disclosure. Reference is also made to FIG. 7D, which shows the views of FIG. 7C reduced in size, alongside corresponding anatomical views 791, 792, 793, 794, 795, 796 of a heart 750, according to some exemplary embodiments of the present disclosure.

Arrows 730 may be understood as indicating rotation of GUI widget 700 and/or heart 750 by about 90° between the view at the base of each arrow, and the view at the tip. The rotation may be understood as a 90° roll, comprising rotation of the surface portion nearest the viewer's position to a perpendicular orientation on the side of the rotated GUI widget 700 which is away from the arrow tip.

Heart view 791 and GUI widget view 741 correspond to the view of FIGS. 7A-7B. Both the light-shaded right atrium 752 and dark-shaded left atrium 754 are clearly visible in the anatomical view 791.

Heart view 793 shows a conventional, top side up ventral view of a heart 750, with the right atrium 752 clearly visible, but the left atrium largely hidden. The corresponding view 743 of the GUI widget 700, however, shows both atria clearly. Moreover, it is easy to tell by glancing at views 741 and 743 how the two views relate to one another, since most of features remain plainly visible in each. In heart views 791, 793, the changing orientation leads to radical changes in apparent shape, and/or changes in which anatomical features are visible. Similar observations apply to comparisons involving views of the other orientations. It can be understood that the difference in ease of comprehension potentially becomes still more pronounced when differential shading of the heart views (shown herein primarily for purposes of explanation) is removed and/or replaced with shading serving some different purpose.

Another potential advantage of the GUI widget 700 is seen most particularly in connection by consideration of the sequence of views 742, 743, and 744. Shading of the GUI widget as viewed from the side of left atrium (view 742) is almost completely dark (using the shading conventions illustrated), while shading as viewed from the opposite side (view 744) is almost completely light. About equal balance between the two shadings is seen in ventral view 743. These gross differences can be discerned even in peripheral vision, which is a potential advantage for an operator whose visual attention is focused on a nearby anatomical display.

The anatomical views 791, 792, 793, 794, 795, 796 of heart 750 are shown all at the same scale. However, it should be understood that the same orientation information is shown, in some embodiments, as the anatomical view is magnified. Optionally, some indication of such scale changes are optionally also provided on GUI widget 700. For example, a region of viewing indicator (a rectangle, for example) is optionally superimposed on the GUI widget 700 to indicate which part of the represented anatomy is being closely inspected. Optionally, a view from within an organ (for example, from within an atrium) is indicated by modification of the GUI widget 700, for example, by suppressing display of the GUI widget portions representing anatomy which is "behind" the viewing port of the anatomy.

Indicators for Monitoring of Lesion Status

Reference is now made to FIGS. 8A-8E, which illustrate a display for indicating lesioning status, including contact force, to a user, according to some exemplary embodiments.

FIGS. 8A-8E comprise an artificially rendered image of an ablation probe 802 and its position relative to tissue 805 near to which ablation probe 802 is positioned for ablation. Optionally, the rendering is in color similar to the vital color of the tissue (black and white is shown for purposes of illustration). In some embodiments, the rendering includes a visual indication of contact pressure between the tissue 805 and the electrode 802 comprising an indented region 804. For example, indented region 804 is shown more strongly deflected in FIG. 8B than in FIG. 8A (and not deflected at all in FIG. 8D), providing an indication of relative contact force. Optionally, the depth to which indented region 804 is actually shown indented is variable depending, for example, on a measured contact force and/or contact quality value.

Figure 8A:
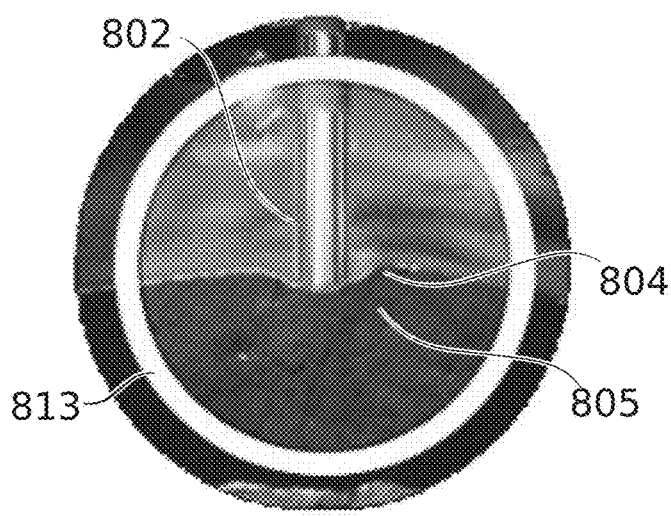
FIGS. 8A-8E illustrate a display for indicating lesioning status, including contact force, to a user, according to some exemplary embodiments.
Figure 8B:
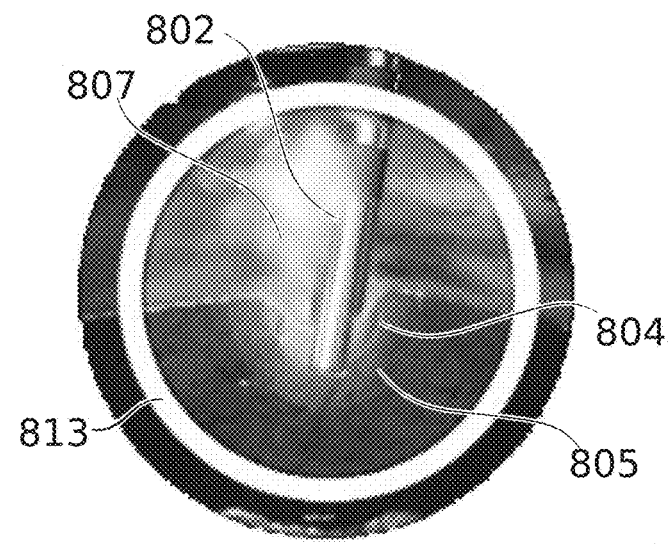
Figure 8C:
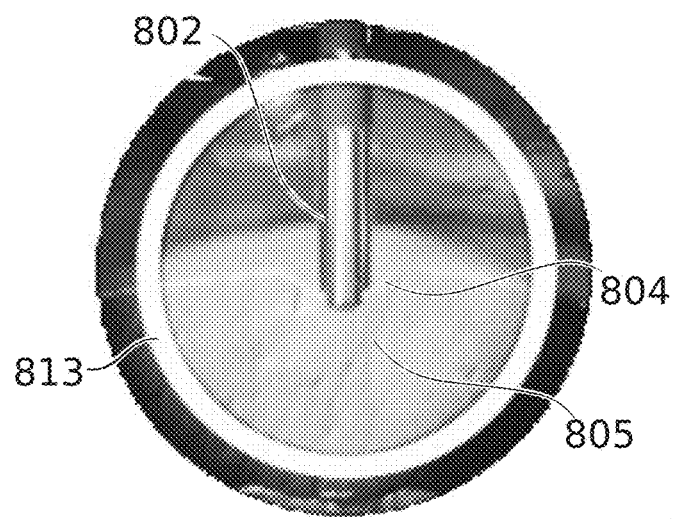
Figure 8D:
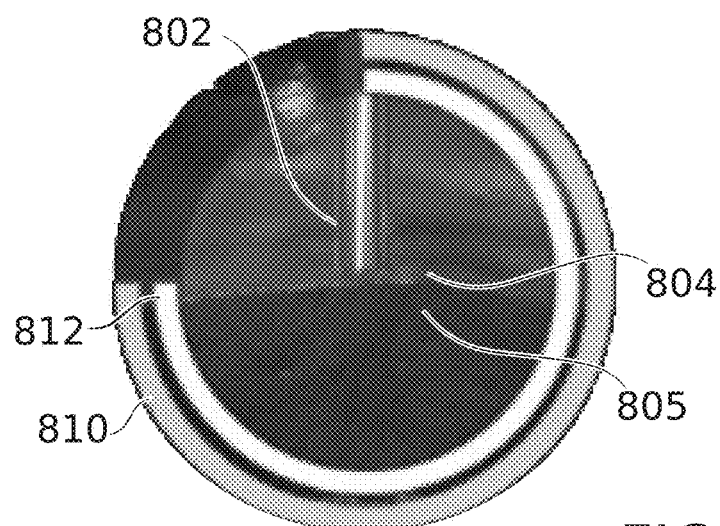
Figure 8E:
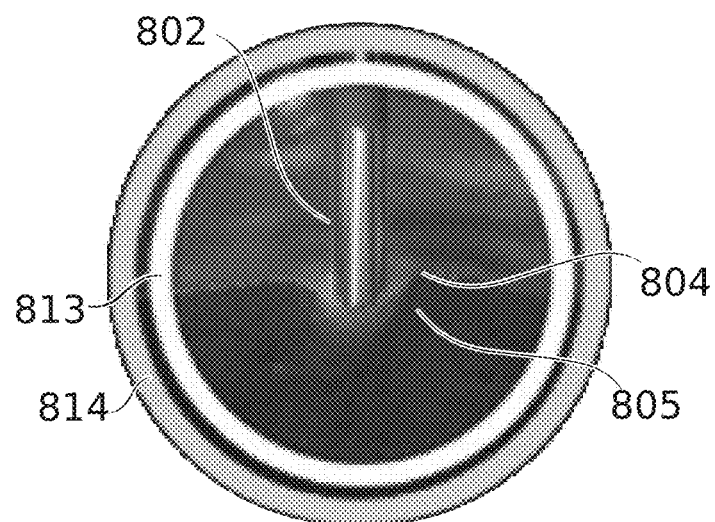

In some embodiments, an estimate of a quality of the lesion which would be and/or is being formed at a current site of contact is provided by a visual indication, such as circle 813. In FIGS. 8D-8E, additional indication 810, 812, and 814 are also shown, indicating full or partial degrees of transmural lesioning as estimated based on pre- or post-lesion measurements. More details of such indications used for one or both of pre- and post-lesioning tissue assessment for transmurality of a lesion are discussed, for example, in relation to FIG. 9.

In some embodiments, one or more additional indications are provided as part of the rendered image which provide an indication of how lesioning is proceeding. For example, in FIG. 8B, "steam" is shown arising from the lesion point. Optionally, this is an indication that temperature has reached (and/or is maintained at) a certain threshold. The threshold may be, for example, a threshold at which lesioning occurs, a threshold above which a danger of effects such as steam pop or charring occurs, or another threshold. In FIG. 8C, tissue 805 is shown relatively bleached in color, which optionally serves as an indication of the current estimated extent of lesioning.

Figure 9:
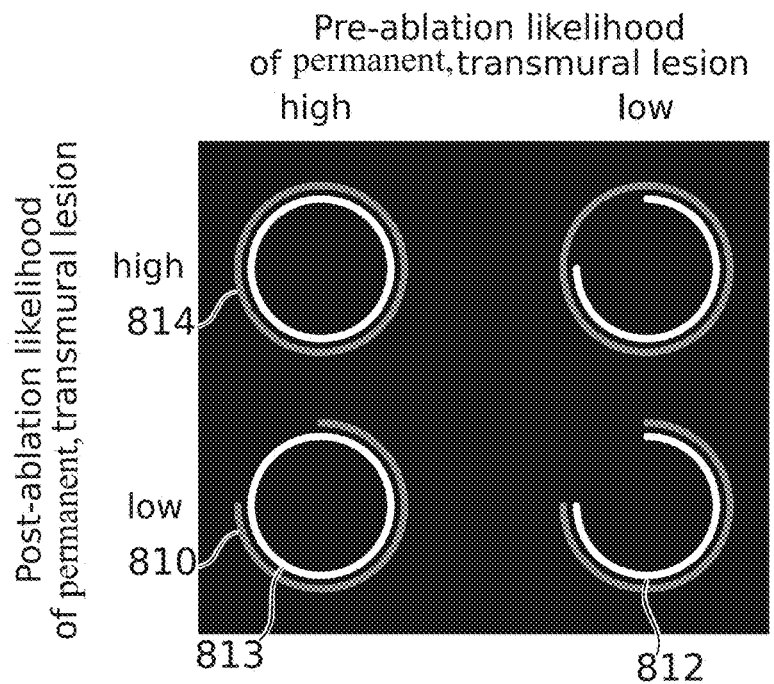
FIG. 9 illustrates display elements which are optionally used to indicate estimated transmurality of a lesion to a user, based on pre- and post-lesioning dielectric property measurements.

Reference is now made to FIG. 9, which illustrates display elements 810, 812, 813, 814 which are optionally used to indicate estimated transmurality of a lesion to a user, based on pre- and post-lesioning dielectric property measurements.

In some embodiments, estimated transmurality is communicated to a user by the use of a simplified graphical element. The elements of FIG. 9 take the form of complete circles 813, 814, to indicate a positive estimate of lesion transmurality, and the form of incomplete circles 812, 810 (e.g., ¾ circles) to indicate a negative estimate of lesion transmurality. Optionally, inner circles 812, 813 are used to indicate estimates based on pre-lesioning measurements. Optionally, outer circles 810, 814 are used to indicate estimates based on post-lesioning measurements.

It is expected that during the life of a patent maturing from this application many relevant transcatheter treatments will be developed; the scope of the term "transcatheter delivery of a disease treatment" is intended to include all such new technologies a priori.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of characterizing contact quality between a target tissue and an intra-body probe, during an interventional procedure, comprising a plurality of electrodes, the method comprising:
   measuring, at a plurality of electrical field frequencies and by the plurality of electrodes of the intra-body probe, a plurality of dielectric properties of the environment of electrodes of the intra-body probe, using an electrical circuit comprising the target tissue and the plurality of electrodes of the intra-body probe;
   and
   characterizing contact quality between the target tissue and the intra-body probe by mapping the plurality of dielectric properties, measured at the plurality of frequencies by the plurality of electrodes, to a value in a range indicating a measure of contact quality.

2. The method of claim 1, wherein the intra-body probe is flexible and carries said plurality of electrodes, and the flexibility of the probe allows the plurality of electrodes to be positioned along a portion of the target tissue.

3. The method of claim 1, wherein the intra-body probe makes a plurality of simultaneous contacts with the target tissue, and the characterizing comprises separately characterizing each of the plurality of simultaneous contacts.

4. The method of claim 3, wherein the intra-body probe comprises an ablation electrode, and wherein the method comprises operating the ablation electrode to ablate at each of the plurality of simultaneous contacts under separate control, based on the corresponding characterizing of contact.

5. The method of claim 1, wherein the characterization of the contact comprises mapping of the measured dielectric properties to a mapped value within a range of values characterizing the contact quality, and the mapped value comprises an index characterizing contact quality of a particular electrode.

6. The method of claim 1, wherein the value in the range indicating a measure of contact quality represents a contact force equivalent.

7. The method of claim 6, wherein the mapping to said mapped value representing said equivalent force of contact is substantially independent of an angle of contact between the probe and the surface of the target tissue.

8. The method of claim 7, wherein the equivalent force of contact changes by less than 10% through a range of angles of contact, and the range of angles of contact is within 45° of a central angle of contact.

9. The method of claim 1, wherein the intra-body probe comprises all the electrodes defining the electrical circuit.

10. The method of claim 1, wherein the characterizing comprises estimation of an equivalent force of contact of the probe with a surface of the target tissue, and the method comprises providing a user feedback indicating the equivalent force of contact.

11. The method of claim 1, comprising operating an ablation electrode based on the characterization of the contact and wherein the operating of the ablation electrode is gated to occur only when the characterized contact is within a predetermined range.

12. The method of claim 11, wherein the characterizing contact is performed iteratively during operating of the ablation electrode.

13. The method of claim 1, comprising operating an ablation electrode, wherein the operating of the ablation electrode is based on an estimated contact force of the characterized contact, such that at least one of an ablation power, a duration of ablation, a selection of an electrode, and a frequency of ablation energy, is selected based on the estimated contact force.

14. The method of claim 1, wherein the characterizing comprises evaluating a risk of perforation of the target tissue by the probe, and the method comprising providing a user feedback indicating the risk of perforation.

15. The method of claim 1, wherein the characterizing contact is based on a data structure mapping measured dielectric properties to a characterization of contact with the target tissue.

16. The method of claim 15, wherein the data structure comprises machine-learned associations applicable to the measured dielectric properties to convert them to the characterization of contact with the target tissue.

17. The method of claim 1, wherein said electrodes comprise at least one non-tip electrode and at least one tip electrode, between which said measuring is performed.

18. The method of claim 1, wherein most of said electrodes contact blood and not said target tissue during said measuring.

19. The method of claim 1, wherein said mapping comprises mapping values measured at different electric field frequencies to a single value indicating a measure of the contact quality.

20. The method of claim 1, comprising determining an angle of contact between the intra-body probe and the tissue using said dielectric measurements.

21. The method of claim 1, wherein mapping comprises producing a time varying contact quality indication.

22. The method of claim 1, wherein mapping comprises producing an instantaneous contact quality.

23. The method of claim 1, wherein mapping comprises weighting measurements at multiple frequencies.

24. A device for ablation of a target tissue based on dielectric contact quality of an intra-body ablation probe with the target tissue, comprising:
the intra-body ablation probe, including a plurality of electrodes;
an electrical field measurement device, configured to measure dielectric properties in the environment of the plurality of electrodes based on signals sensed by a plurality of electrode pairs of the plurality of electrodes and at a plurality of frequencies; and
a contact characterization module, configured to characterize contact between the intra-body ablation probe and the target tissue, based on the dielectric properties measured by the electrical field measurement device at the plurality of frequencies.

25. The device of claim 24, wherein the contact characterization module comprises a data structure mapping the dielectric properties to characterization of contact.

26. The device of claim 25, wherein the data structure comprises machine-learned associations applicable to the measured dielectric properties to convert them to the characterization of contact with the target tissue.

27. The device of claim 24, comprising a display configured to display the characterized contact as an estimate of contact force.

28. The device of claim 24, wherein the intra-body probe is flexible and, and the flexibility of the probe allows the plurality of electrodes to be positioned along a portion of the target tissue.

29. The device of claim 28, wherein the intra-body probe is configured to make a plurality of simultaneous contacts with the target tissue, and the characterizing comprises separately characterizing each of the plurality of simultaneous contacts.

30. The device of claim 24, wherein the intra-body probe is configured to make a plurality of simultaneous contacts with the target tissue, and the characterizing comprises separately characterizing each of the plurality of simultaneous contacts.

31. The device of claim 24, further comprising at least one processor configured to gate the operation of an ablation electrode to occur only when the characterized contact is within a predetermined range.

32. The device of claim 24, wherein the contact characterization module is configured to estimate an equivalent force of contact independently of an angle of contact between the probe and the surface of the target tissue.

33. The device of claim 32, wherein the equivalent force of contact changes by less than 10% through a range of angles of contact, and the range of angles of contact is within 45° of a central angle of contact.

34. The device of claim 24, wherein electrodes comprise at least one non-tip electrode and at least one tip electrode, between which said measuring is performed.

35. The device of claim 24, wherein at least one of said pairs generates an electric field and one of said pairs senses said electric field.

36. The method of claim 24, wherein said contact characterization module maps a plurality of measured values, including measurements at a plurality of frequencies, to a single value indicating a measure of the contact quality.

* * * * *